US011733191B2

(12) United States Patent
Balijepalli et al.

(10) Patent No.: US 11,733,191 B2
(45) Date of Patent: Aug. 22, 2023

(54) CLOSED-LOOP CONTROLLED CHEMICAL APPARATUS

(71) Applicant: Government of the United States of America, as represented by the Secretary of Commerce, Gaithersburg, MD (US)

(72) Inventors: Arvind Kumar Balijepalli, Washington, DC (US); Curt Andrew Richter, Olney, MD (US); Son Truong Le, Germantown, MD (US)

(73) Assignee: GOVERNMENT OF THE UNITED STATES OF AMERICA, AS REPRESENTED BY THE SECRETARY OF COMMERCE, Gaithersburg, MD (US)

( * ) Notice: Subject to any disclaimer, the term of this patent is extended or adjusted under 35 U.S.C. 154(b) by 395 days.

(21) Appl. No.: 17/029,999

(22) Filed: Sep. 23, 2020

(65) Prior Publication Data

US 2021/0088463 A1 Mar. 25, 2021

Related U.S. Application Data

(60) Provisional application No. 62/904,141, filed on Sep. 23, 2019.

(51) Int. Cl.
*G01N 27/12* (2006.01)
*G01N 33/483* (2006.01)
(Continued)

(52) U.S. Cl.
CPC ......... *G01N 27/12* (2013.01); *A61B 5/14546* (2013.01); *A61B 5/4088* (2013.01);
(Continued)

(58) Field of Classification Search
CPC .......... G01N 27/4145; G01N 33/54373; B01L 3/502715; B01L 2200/027
See application file for complete search history.

(56) References Cited

U.S. PATENT DOCUMENTS 4,879,517 A * 11/1989 Connery ............ G01N 27/4148
324/71.5
10,385,377 B2 8/2019 Takechi et al.
(Continued)

OTHER PUBLICATIONS

Zafar, S., et al., "Silicon Nanowire Field Effect Transistor Sensors with Minimal Sensor-to-Sensor Variations and Enhanced Sensing Characteristics", ACS Nano, 2018, p. 6577-6587, vol. 12.
(Continued)

*Primary Examiner* — Jermele M Hollington
*Assistant Examiner* — Temilade S Rhodes-Vivour
(74) *Attorney, Agent, or Firm* — Office of Chief Counsel for National Institute of Standards and Technology

(57) ABSTRACT

A closed-loop controlled chemical apparatus includes: a compound sensor including: an analyte sensor and that: produces, by the analyte sensor, a voltage signal; a reference sensor in electrical communication with the analyte sensor; a transistor including a gate terminal such that a drain current of the transistor is maintained at a constant value and operated at an optimal transduction condition of peak sensitivity and minimum noise of the transistor; a feedback controller in electrical communication with the transistor and that: receives a transduction signal; determining a deviation of the transduction signal from a setpoint, the setpoint determined by transfer characteristics of the transistor; produces the feedback control signal that minimizes the deviation of the transduction signal from the based on a control model; and communicates the feedback control signal to the reference sensor for suppression of electrical
(Continued)

noise fluctuations in the closed-loop controlled chemical apparatus.

20 Claims, 20 Drawing Sheets

(51) Int. Cl.
    *A61B 5/145*       (2006.01)
    *A61K 38/16*      (2006.01)
    *A61B 5/00*        (2006.01)

(52) U.S. Cl.
    CPC .......... *A61B 5/4839* (2013.01); *A61B 5/7203* (2013.01); *A61K 38/16* (2013.01); *G01N 33/483* (2013.01)

(56) References Cited

U.S. PATENT DOCUMENTS

| | | | |
|---|---|---|---|
| 2012/0078071 A1* | 3/2012 | Bohm | A61B 5/14532 600/345 |
| 2016/0238553 A1* | 8/2016 | Shachar | G01N 27/4145 |
| 2017/0350882 A1* | 12/2017 | Lin | G01N 33/54353 |
| 2019/0246959 A1* | 8/2019 | Ionescu | A61B 5/1477 |
| 2019/0369044 A1* | 12/2019 | Chang | G01N 27/4146 |

OTHER PUBLICATIONS

Johnson, K.S., et al., "Deep-Sea DuraFET: A Pressure Tolerant pH Sensor Designed for Global Sensor Networks", Analytical Chemistry, 2016, p. 3249-3256, vol. 88.

Martz, T.R., et a., "Testing the Honeywell Durafet® for seawater pH applications", Limnology and Oceanography: Methods, 2010, p. 172-184, vol. 8.

Ahlijanian, M.K., et al., "Hyperphosphorylated tau and neurofilament and cytoskeletal disruptions in mice overexpressing human p25, an activator of cdk5", PNAS, 2000, p. 2910-2915, vol. 97 No. 6.

Binukumar, B.K., et al., "TFP5, a Peptide Derived from p35, a Cdk5 Neuronal Activator, Rescues Cortical Neurons from Glucose Toxicity", Journal of Alzheimer's Disease, 2014, p. 899-909, vol. 39 No. 4.

Bonda, D.J., et al., "Oxidative stress in Alzheimer disease: A possibility for prevention", Neuropharmacology, 2010, p. 290-294, vol. 59.

Cardone, A., et al., "Computational study of the inhibitorymechanism of the kinaseCDK5 hyperactivity by peptide p5 and derivation of a pharmacophore", Journal of Computer-Aided Molecular Design, 2016, p. 513-521, vol. 30.

Dai, X., et al., "Modularized Field-Effect Transistor Biosensors", Nano Letters, 2019, p. 6658-6664, vol. 19.

Fang, J., et al., "Discovery of Multitarget-Directed Ligands against Alzheimer's Disease through Systematic Prediction of Chemical-Protein Interactions", Journal of Chemical Information and Modeling, 2015, p. 149-164, vol. 55.

Finley, J.W., et al., "A Perspective on *Crocus sativus* L. (Saffron) Constituent Crocin: A Potent Water-Soluble Antioxidant and Potential Therapy for Alzheimer's Disease", Journal of Agricultural and Food Chemistry, 2017, p. 1005-1020, vol. 65.

Helal, C.J., et al., "Discovery and SAR of 2-aminothiazole inhibitors of cyclin-dependent kinase 5/p25 as a potential treatment for Alzheimer's disease", Bioorganic and Medicinal Chemistry Letters, 2004, p. 5521-5525, vol. 14.

Helal, C.J., et al., "Potent and cellularly active 4-aminoimidazole inhibitors of cyclin-dependent kinase 5/p25 for the treatment of Alzheimer's disease", Bioorganic and Medicinal Chemistry Letters, 2009, p. 5703-5707, vol. 19.

Knockaert, M., et al., "Intracellular Targets of Paullones", The Journal of Biological Chemistry, 2002, p. 25493-25501, vol. 277 No. 28.

Lee, M-S., et al., "Neurotoxicity induces cleavage of p35 to p25 by calpain", Nature, 2000, p. 360-364, vol. 405.

Nikolic, M., et al., "The cdk5/p35 kinase is essential for neurite outgrowth during neuronal differentiation", Genes and Development, 1996, p. 816-825.

Noble, W., et al., "Cdk5 Is a Key Factor in Tau Aggregation and Tangle Formation In Vivo", Neuron, 2003, p. 555-565, vol. 38.

Ohshima, T., et al., "Targeted disruption of the cyclin-dependent kinase 5 gene results in abnormal corticogenesis, neuronal pathology and perinatal death", Proc. Natl. Acad. Sci., 1996, p. 11173-11178, vol. 93.

Patrick, G.N., et al., "Conversion of p35 to p25 deregulates Cdk5 activity and promotes neurodegeneration", Nature, 1999, p. 615-622, vol. 402.

Persson, T., et al., "Oxidative Stress in Alzheimer's Disease: Why Did Antioxidant Therapy Fail?", Oxidative Medicine and Cellular Longevity, 2014, Article ID Article ID 427318, DOI: https://doi.org/10.1155/2014/427318.

Ronchi, S., et al., "Single-Cell Electrical Stimulation Using CMOS-Based High-Density Microelectrode Arrays", Frontiers in Neuroscience, 2019, vol. 13 Article. 208.

Shah, K., et al., "Tale of the Good and the Bad Cdk5: Remodeling of the Actin Cytoskeleton in the Brain", Mol Neurobiol, 2018, p. 3426-3438, vol. 55.

Shupp, A., et al., "Biological functions of CDK5 and potential CDK5 targeted clinical treatments", Oncotarget, 2017, p. 17373-17382, vol. 8 No. 10.

Sundaram, J.R., et al., "Specific Inhibition of p25/Cdk5 Activity by the Cdk5 Inhibitory Peptide Reduces Neurodegeneration In Vivo", The Journal of Neuroscience, 2013, p. 334-343, vol. 33 No 1.

Tan, T.C., et al., "Cdk5 is essential for synaptic vesicle endocytosis", Nature Cell Biology, 2003, p. 701-710, 1-7, vol. 5 No. 8.

Utreras, E., et al., "Molecular roles of Cdk5 in pain signaling", Drug Discovery Today: Therapeutic Strategies, 2009, p. 105-111, vol. 6 No 3.

Zheng, Y-L., et al., "A Cdk5 inhibitory peptide reduces tau hyperphosphorylation and apoptosis in neurons", The EMBO Journal, 2005, p. 209-220, vol. 24.

Zheng, Y-L., et al., "A 24-Residue Peptide (p5), Derived from p35, the Cdk5 Neuronal Activator, Specifically Inhibits Cdk5-p25 Hyperactivity and Tau Hyperphosphorylation", The Journal of Biological Chemistry, 2010, p. 34202-34212, vol. 285 No. 44.

\* cited by examiner

| pH | 6.72 | 6.81 | 6.88 | 6.96 | 7.05 |
|---|---|---|---|---|---|
| $nFET_{open-loop}$ | 17.7 | 27.1 | 24.0 | 18.6 | 25.4 |
| $nFET_{PID}$ | 6.0 | 6.6 | 8.0 | 7.3 | 7.6 |
| $dg2DFET$ | 3.5 | 2.6 | 5.8 | 5.0 | 2.3 |

FIG. 11

CLOSED-LOOP CONTROLLED CHEMICAL APPARATUS

CROSS REFERENCE TO RELATED APPLICATIONS

The application claims priority to U.S. Provisional Patent Application Ser. No. 62/904,141 filed Sep. 23, 2019, the disclosure of which is incorporated herein by reference in its entirety.

STATEMENT REGARDING FEDERALLY SPONSORED RESEARCH

This invention was made with United States Government support from the National Institute of Standards and Technology (NIST), an agency of the United States Department of Commerce. The Government has certain rights in the invention. Licensing inquiries may be directed to the Technology Partnerships Office, NIST, Gaithersburg, Md., 20899; voice (301) 975-2573; email tpo@nist.gov; reference NIST Docket Number 19-057US1.

BRIEF DESCRIPTION

Disclosed is a closed-loop controlled chemical apparatus comprising: a compound sensor comprising: an analyte sensor and that: produces, by the analyte sensor, a voltage signal that varies in response to an analyte that electrically perturbs the analyte sensor, such that an electrical perturbation changes the voltage signal from a target voltage, the voltage signal referenced to a reference voltage provided by a reference sensor through a composition comprising the analyte; the reference sensor in electrical communication with the analyte sensor through the composition and that: receives a feedback control signal from a feedback controller; and actively nulls the difference between the voltage signal and the target voltage when the analyte sensor is perturbed by the analyte to maintain the analyte sensor at the target voltage for suppression of electrical noise fluctuations in the closed-loop controlled chemical apparatus that affect the voltage signal; a transistor comprising a gate terminal that is in electrical communication with the analyte sensor, such that: the gate terminal receives a gate potential such that a drain current of the transistor is maintained at a constant value in response to receipt of the feedback control signal by the reference sensor, such that the transistor is operated at an optimal transduction condition comprising peak sensitivity of the transistor and minimum noise of the transistor based on the reference sensor; the feedback controller in electrical communication with the transistor and that: receives a transduction signal; determining a deviation of the transduction signal from a setpoint, the setpoint determined by transfer characteristics of the transistor; produces the feedback control signal that minimizes the deviation of the transduction signal from the based on a control model; and communicates the feedback control signal to the reference sensor for suppression of electrical noise fluctuations in the closed-loop controlled chemical apparatus.

Disclosed is a process for performing closed-loop control of a closed-loop controlled chemical apparatus, the process comprising: producing, by the analyte sensor, the target voltage; contacting the analyte sensor and the reference sensor with the composition; electrically perturbing, by the analyte in the composition, the analyte sensor; changing, in response to the electrical perturbation, the voltage signal from the target voltage; receiving, by the reference sensor, the feedback control signal from the feedback controller; actively nulling the difference between the voltage signal and the target voltage when the analyte sensor is electrically perturbed by the analyte to maintain the analyte sensor at the target voltage for suppression of electrical noise fluctuations in the closed-loop controlled chemical apparatus that affect the voltage signal; receiving, by the gate terminal of the transistor, the gate potential such that the drain current of the transistor is maintained at the constant value in response to receipt of the feedback control signal by the reference sensor, wherein the is operated at an optimal transduction condition comprising peak sensitivity of the transducer and minimum noise of the transistor based on the feedback control signal; receiving, by the feedback controller, the transduction signal; determining the setpoint from transfer characteristics of the transistor; determining, by the feedback controller, the deviation of the transduction signal from the setpoint; producing, by the feedback controller, the feedback control signal that minimizes the deviation of the transduction signal from the setpoint based on the control model; and communicating the feedback control signal from the feedback controller to the reference sensor and suppressing the electrical noise fluctuations to perform closed-loop control of the closed-loop controlled chemical apparatus.

BRIEF DESCRIPTION OF THE DRAWINGS

The following description should not be considered limiting in any way. With reference to the accompanying drawings, like elements are numbered alike.

FIG. 11 shows pH resolution of phosphate buffered saline solutions measured at a bandwidth of 10 Hz;

DETAILED DESCRIPTION

Figure 1:
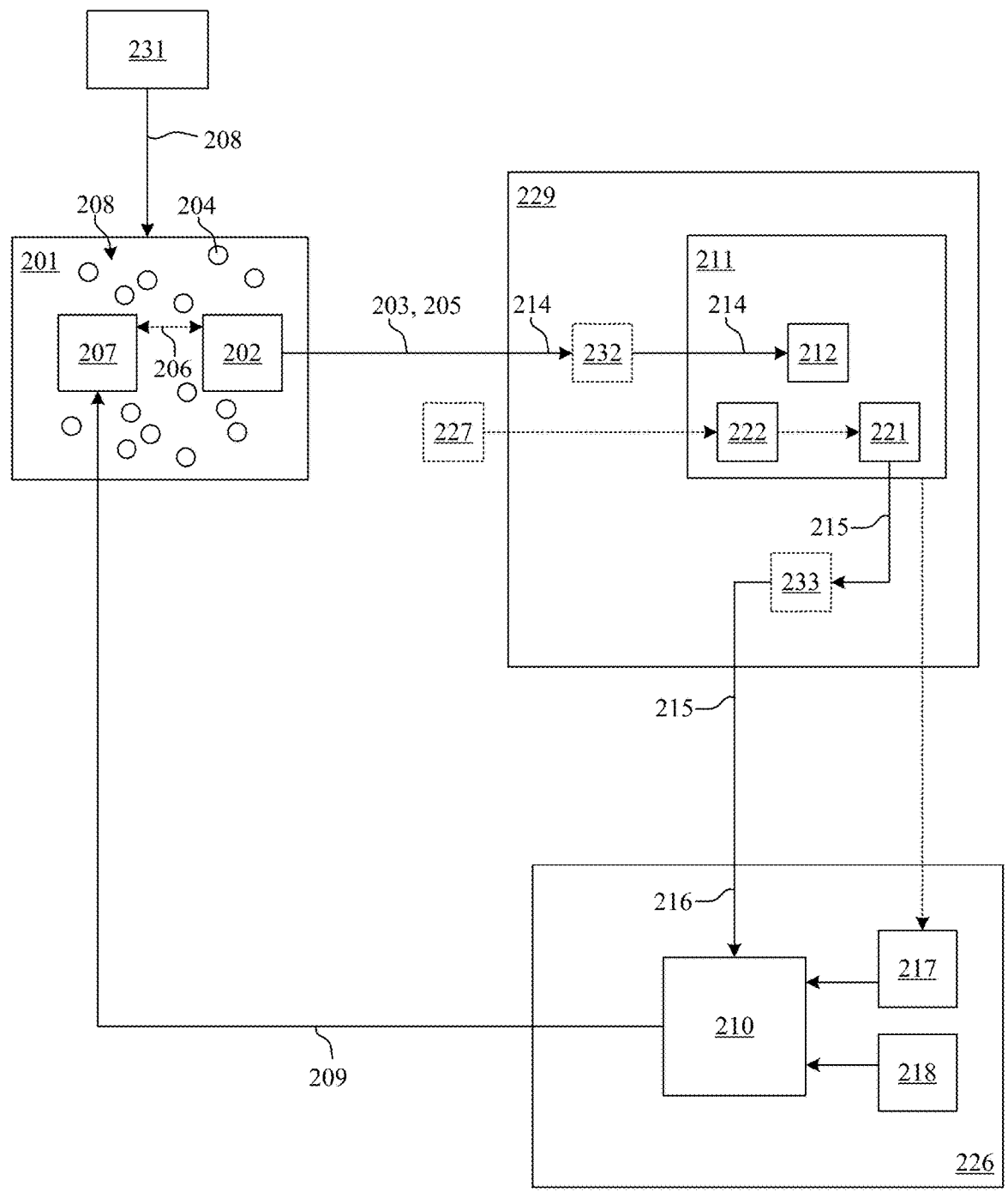
FIG. 1 shows a closed-loop controlled chemical apparatus.

A detailed description of one or more embodiments is presented herein by way of exemplification and not limitation.

It has been discovered that a closed-loop controlled chemical apparatus and processes herein provide readout elements for a biosensor to achieve about a three-fold improvement in pH resolution over conventional ion-sensitive field-effect transistors (ISFETs). The closed-loop controlled chemical apparatus is operated under closed-loop control, actively nulling any input to a gate terminal of a transistor from charge fluctuations at a sensing surface of an analyte sensor. The improved pH resolution was realized while as the closed-loop controlled chemical apparatus were operated in a remote configuration with a pH sensing surface off-chip and connected electrically to a gate terminal of a transistor. The closed-loop controlled chemical apparatus has a sensitivity and resolution that measured activity of a pathological form of kinase Cdk5, an enzyme implicated in Alzheimer's disease, and demonstrated effectiveness of a polypeptide, p5, as a therapeutic agent in restoring non-pathologic function of Cdk5. Accordingly, the closed-loop controlled chemical apparatus and processes herein provide drug discovery and clinical diagnostics.

In an embodiment, with reference to FIG. 1, FIG. 2, FIG. 3, and FIG. 4, closed-loop controlled chemical apparatus 200 includes: compound sensor 201 including: analyte sensor 202 and that: produces, by analyte sensor 202, voltage signal 203 that varies in response to analyte 204 that electrically perturbs analyte sensor 202, such that an electrical perturbation changes voltage signal 203 from target voltage 205, voltage signal 203 referenced to reference voltage 206 provided by reference sensor 207 through composition 208 comprising analyte 204; reference sensor 207 in electrical communication with analyte sensor 202 through composition 208 and that: receives feedback control signal 209 from feedback controller 210; and actively nulls the difference between the voltage signal 203 and the target voltage 205 when analyte sensor 202 is perturbed by analyte 204 to maintain analyte sensor 202 at target voltage 205 for suppression of electrical noise fluctuations in closed-loop controlled chemical apparatus 200 that affect voltage signal 203; transistor 211 including gate terminal 212 that is in electrical communication with analyte sensor 202, such that: gate terminal 212 receives gate potential 214 such that drain current 215 of transistor 211 is maintained at a constant value in response to receipt of feedback control signal 209 by reference sensor 207, such that transistor 211 is operated at an optimal transduction condition including peak sensitivity of transistor 211 and minimum noise of transistor 211 based on feedback control signal 209; feedback controller 210 in electrical communication with transistor 211 and that: receives transduction signal 216; determines a deviation of transduction signal 216 from setpoint 217, setpoint 217 determined by transfer characteristics of transistor 211; produces feedback control signal 209 that minimizes the deviation of transduction signal 216 from setpoint 217 based on control model 218; and communicates feedback control signal 209 to reference sensor 207 for suppression of electrical noise fluctuations in closed-loop controlled chemical apparatus 200.

Advantageously, by using feedback control signal 209 to control reference sensor 207 in combination with analyte sensor 202 and transistor 211, closed-loop controlled chemical apparatus 200 has a pH resolution of $3.5 \times 10^{-3}$ pH units that is more than three times greater than a pH resolution of an ion-sensitive field-effect transistor operated in absence of feedback control signal 209.

In an embodiment, with reference to FIG. 1, transduction signal 216 includes drain current 215 from transistor 211.

Figure 2:
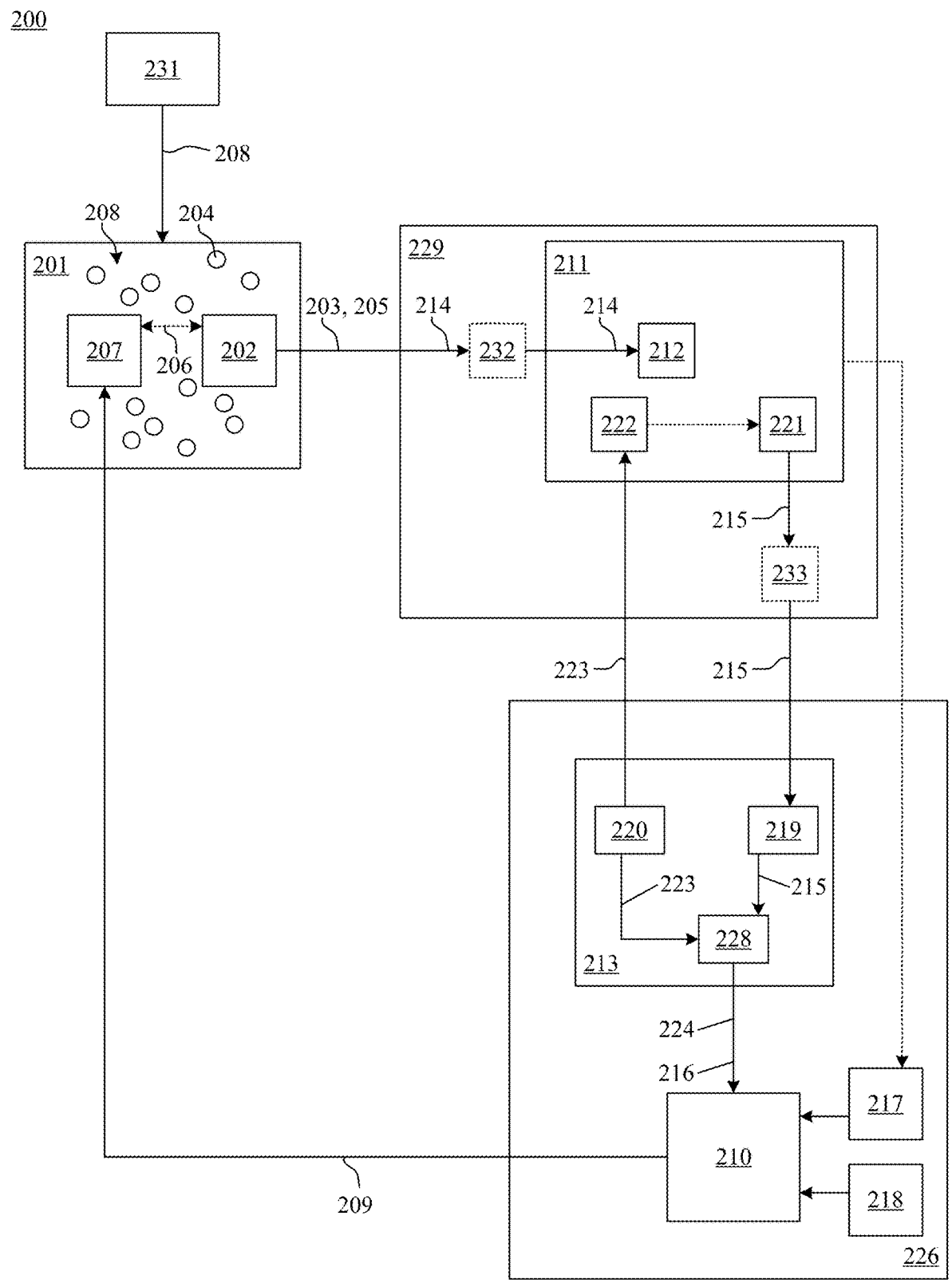
FIG. 2 shows a closed-loop controlled chemical apparatus.
Figure 4:
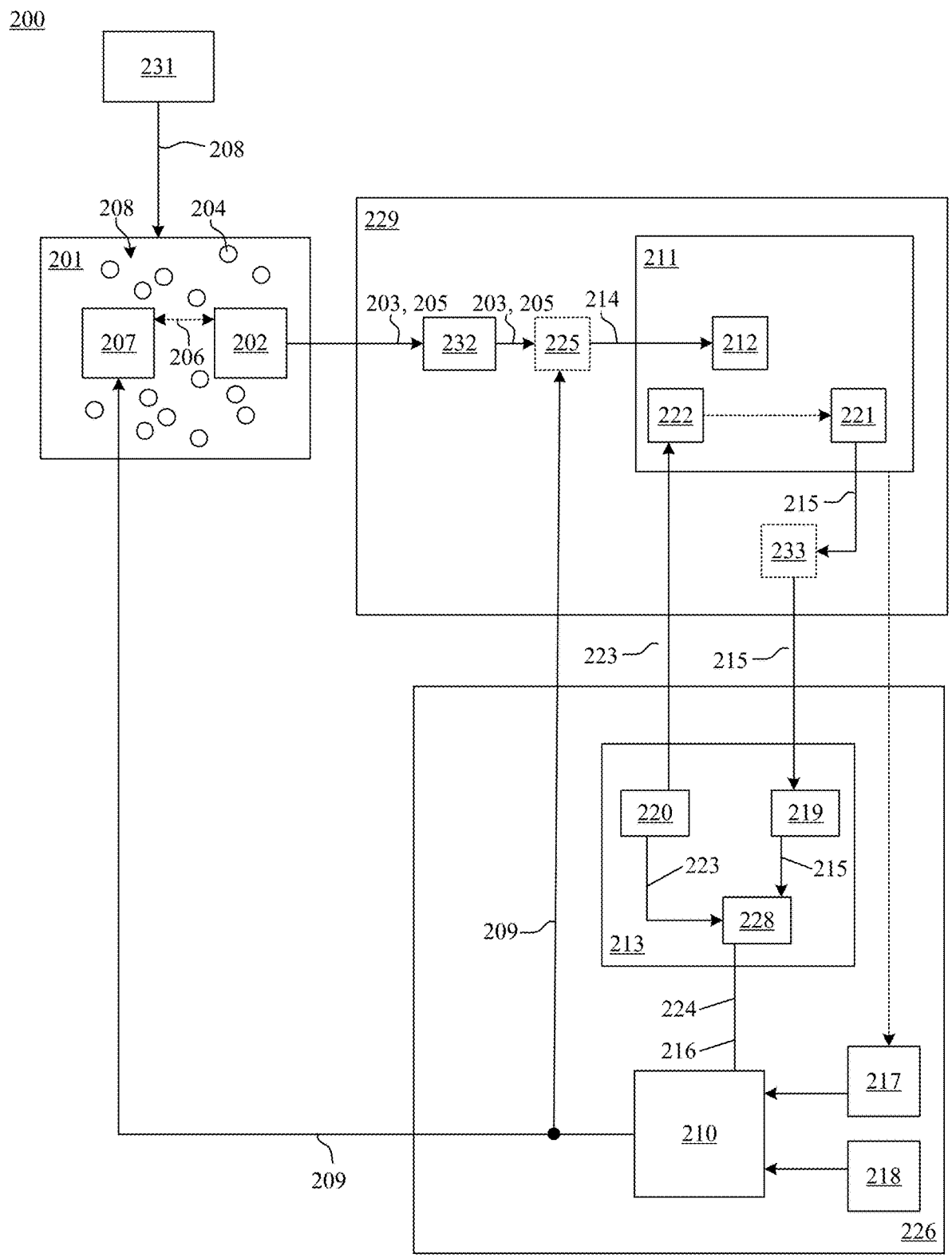
FIG. 4 shows a closed-loop controlled chemical apparatus.

According to an embodiment, with reference to FIG. 2 and FIG. 4, closed-loop controlled chemical apparatus 200 includes phase-sensitive detector 213 (e.g., a lock-in amplifier) in electrical communication with transistor 211 such that: input terminal 219 of phase-sensitive detector 213 is in electrical communication with drain terminal 221 of transistor 211 and that receives drain current 215 from drain terminal 221; and output terminal 220 of phase-sensitive detector 213 is in electrical communication with source terminal 222 of transistor 211 and that communicates oscillating voltage 223 to source terminal 222, such that phase-sensitive detector 213: compares drain current 215 to oscillating voltage 223 and produces direct current signal 224 that is proportional to a phase difference between drain current 215 and oscillating voltage 223; and communicates direct current signal 224 to feedback controller 210 as transduction signal 216.

In an embodiment, with reference to FIG. 1 and FIG. 2, gate potential 214 includes voltage signal 203 from analyte sensor 202.

Figure 3:
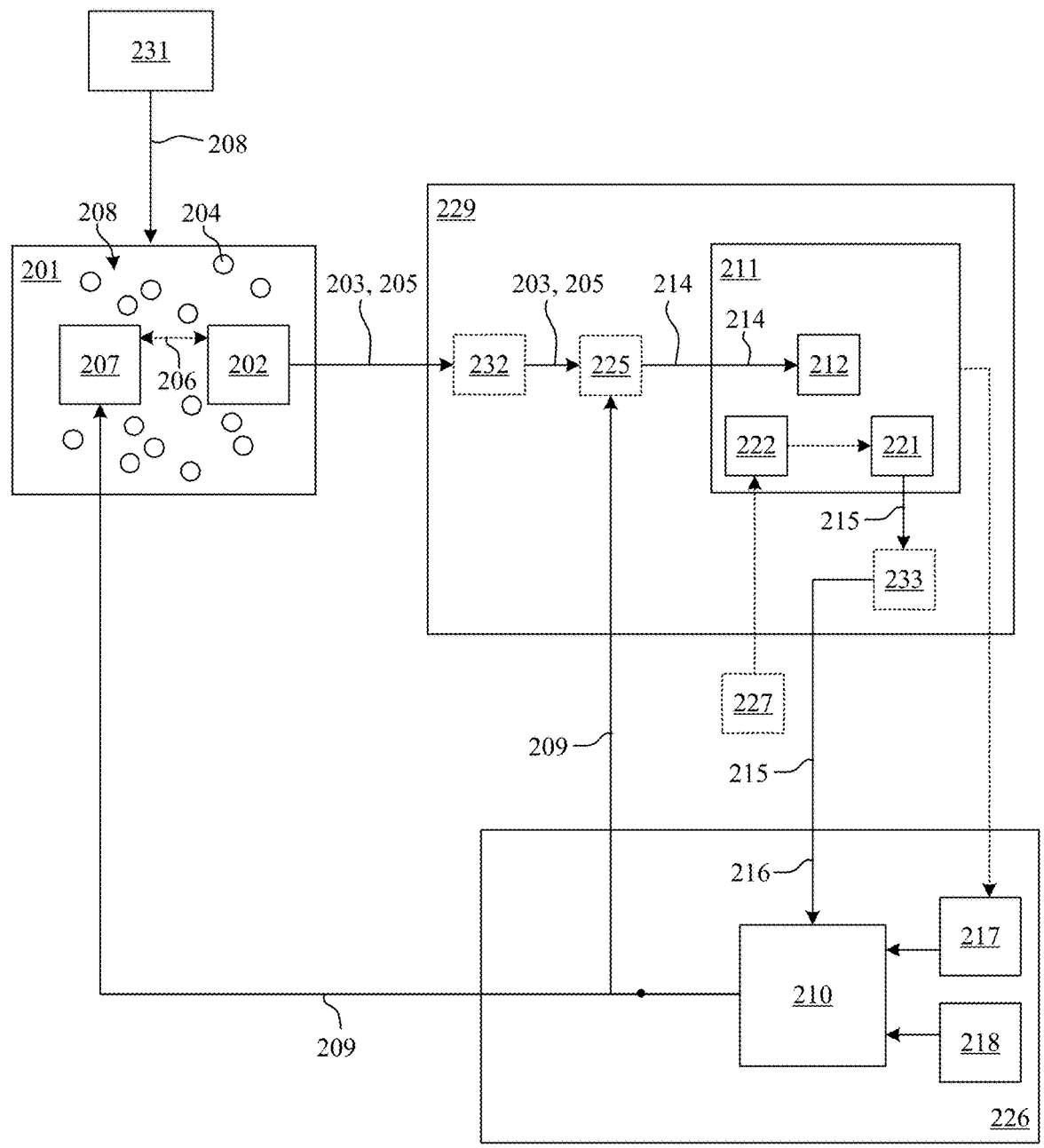
FIG. 3 shows a closed-loop controlled chemical apparatus.

In an embodiment, with reference to FIG. 3 and FIG. 4, closed-loop controlled chemical apparatus 200 includes summer 225 in electrical communication with analyte sensor 202, feedback controller 210, and gate terminal 212 and that: receives feedback control signal 209 from feedback controller 210; receives voltage signal 203 from analyte sensor 202; and sums feedback control signal 209 and voltage signal 203 to produce gate potential 214; and communicates gate potential 214 to gate terminal 212.

Reference sensor 207 and analyte sensor 202 are independent electrodes that can be electrically conductive or capacitively coupled to be in electrical communication with other elements. A size of reference sensor 207 and analyte sensor 202 can be selected so that compound sensor 201 can be disposed in a suitable container for receipt of composition 208 that can be communicated from composition source 231. Composition source 231 can be a macrofluidic or microfluidic flow system or static reservoir. Suitable pumps and delivery conduits (e.g., tubing) can fluidically connect composition source 231 to compound sensor 201 for delivery of composition 208 to compound sensor 201. Flow between composition source 231 and compound sensor 201 can be controlled via devices such as flow meters.

Composition 208 can include analyte 204 as well as other constituents such as solvents, other compounds (e.g., small molecule drugs), excipients, cells, proteins, and the like. Analyte 204 can be any item that electrically perturbs analyte sensor 202 by presence of analyte 204 at analyte sensor 202, including direct contact therebetween or indirect contact such as interaction through an electrical double layer proximate to a surface of analyte sensor 202, wherein the electrical perturbation can occur by a formal electrical charge of analyte 204 or higher order electrical moment of analyte 204 such as a dipole interaction, quadrupole interaction, and the like effecting the electrical perturbation of analyte sensor 202. Exemplary analytes 204 include small molecule drugs, proteins, cells, polymers, inorganic compounds, and the like. A concentration of analyte 204 in composition 208 can be selected as an unknown value of known value, e.g., for calibration of compound sensor 201. In an embodiment, analyte 204 includes a pathological form of a protein. It is contemplated that the protein can be an enzyme implicated in Alzheimer's disease, such as CDK5. In an embodiment, analyte 204 includes a therapeutic agent that restores a nonpathological function of a pathogenic form of a protein.

Analyte sensor 202 produces voltage signal 203 that initially can be at target voltage 205 in an absence of analyte 204 electrically perturbing analyte sensor 202, and changes from target voltage 205 in a presence of analyte 204 that electrically perturbs analyte sensor 202. Target voltage 205 referenced to reference voltage 206 can be a selected value such as the voltage value of reference voltage 206. When analyte sensor 202 is electrically perturbed by analyte 204, the electrical potential of analyte sensor 202 changes from target voltage 205 to voltage signal 203 so that a larger potential difference occurs relative to reference voltage 206. Accordingly, a potential difference between voltage signal 203 and reference voltage 206 is greater than the potential difference between target voltage 205 and reference voltage 206, wherein the magnitude of the potential difference between voltage signal 203 and reference voltage 206 increases as the strength of the electrical perturbation of analyte sensor 202 by analyte 204 increases.

With reference to, e.g., FIG. 1, transducer 229 receive gate potential 214 can be voltage signal 203 or target voltage 205, depending on whether analyte 204 electrically perturbs analyte sensor 202. Transducer 229 includes optional isolator 232 that can be, e.g., a switch to isolate transistor 211 from compound sensor 201. Isolator 232 can be controlled by an external signal, e.g., a TTL voltage from an external source that can be programmatically or user set. Transistor 211 can be of various types such a field-effect transistor (FET, e.g., a silicon FET) that includes gate terminal 212, source terminal 222, and drain terminal 221 in which gate terminal 212 receives gate potential 214 and an amount of drain current 215 (e.g., sourced from power source 227 or from phase-sensitive detector 213) that flows in an active channel between source terminal 222 and drain terminal 221 is determined by the magnitude of voltage of gate potential 214 received at gate terminal 212. Transducer 229 can include amplifier 233 that receives drain current 215 from drain terminal 221 and that amplifies the drain current for communication to signal processor 226.

Signal processor 226 is in electrical communication with transducer 229. Signal processor 226 uses setpoint 217 that is derived a model of the transfer function of transducer 229, particularly operation of transistor 211. It is contemplated that Setpoint 217 is set to operate transistor 211 at its optimum operating point derived from the transfer characteristics of transistor 211. Here, feedback controller 210 (e.g., a proportion-integration-derivative (PID) controller) receives setpoint 217 and control model 218 to determine feedback control signal 209 from transduction signal 216 that can be drain current 215 from drain terminal 221 of transistor 211 or direct current signal 224 from phase-sensitive detector 213. It should be appreciated that control model 218 can have one of many embodiments that approximate dynamics of the measurement system. Control model 218, in conjunction with feedback controller 210, evaluates the difference between transduction signal 216 and setpoint 217 to produce feedback control signal 209 that actively drives transduction signal 216 to setpoint 217.

In some embodiments, signal processor 226 includes phase-sensitive detector 213. Exemplary phase-sensitive detector 213 include a lock-in amplifier that determines a phase difference between oscillating voltage 223 and drain current 215 from output terminal 220 and input terminal 219, respectively. Here, drain current 215 is received from transistor 211 by input terminal 219, and oscillating voltage 223 is provided internally and communicated to source terminal 222 of source terminal 222 via output terminal 220.

Figure 5:
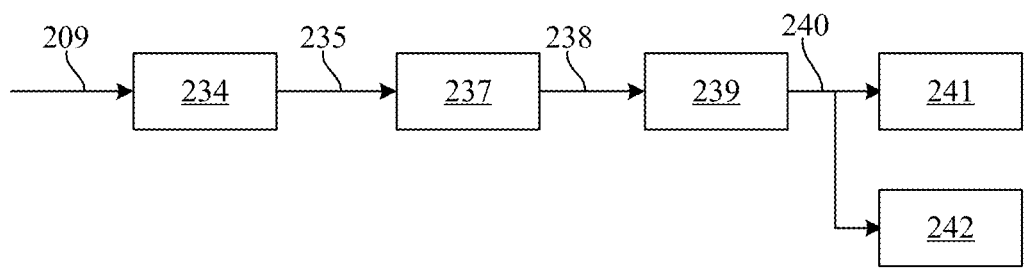
FIG. 5 shows a readout 230 for a closed-loop controlled chemical apparatus.

Feedback control signal 209 is communicated from feedback controller 210 to reference sensor 207 of compound sensor 201. Reference sensor 207 is used to actively null the difference between voltage signal 203 and target voltage 205 caused by analyte 204 through electrical perturbation of analyte sensor 202. In an embodiment, with reference to FIG. 5, feedback control signal 209 also can be communicated from feedback controller 210 to readout 230 that can visually display or store analyte information 240. Readout 230 can include filter 234 that filters feedback control signal 209 and produces filtered signal 235 that is communicated to digitizer 237 that digitizes filtered signal 235 and produces digitized signal 238. Digitized signal 238 is received by data processor 239 that produces analyte information 240 from digitized signal 238. Analyte information 240 can include properties of the analyte type that include individual or some combination of properties such as its concentration in solution determined by the amplitude of the signal, kinetic information pertaining to its interaction with the sensor that further allows discrimination of analyte type from other species in solution, and the like. Display 241 (e.g., a computer monitor) can display analyte information 240, e.g., as a visual image for a user, and data storage 242 (e.g., a server or other non-transitory storage medium) can store analyte information 240.

Closed-loop controlled chemical apparatus 200 can be made in various ways. In an embodiment, a process for making closed-loop controlled chemical apparatus 200 includes electrically connecting compound sensor 201 to transducer 229. Voltage signal 203 from compound sensor 201 communicates analyte information to gate terminal 212 of transistor 211. In another embodiment, isolator 232 isolates transducer 229 from compound sensor 201. Voltage signal 203 modulates drain current 215 of transistor 211 to generate transduction signal 216. Transduction signal 216 is connected electrically to feedback controller 210. In another embodiment, drain current 215 is connected to input terminal 219 of phase-sensitive detector 213. In this embodiment, oscillating voltage 223 is electrically connected to the source terminal of transistor 211. Further, drain current 215 is compared with oscillating voltage 223 using comparator 228 to produce transduction signal 216. Feedback controller 210 is configured to compare transduction signal 216 with setpoint 217. Using control model 218, feedback controller 210 determines feedback control signal 209. Feedback control signal 209 is electrically communicated to reference sensor 207 within compound sensor 201. In another embodiment, feedback control signal 209 is summed with voltage signal 203 by summer 225. Feedback control signal 209 represents the measured output of closed-loop controlled chemical apparatus 200.

It should be appreciated that in making closed-loop controlled chemical apparatus 200 elements thereof are arranged with components to be in communication fluid or electrical communication so that components provide for fluid flow or communication of electrical signals amongst the various electrical components.

Closed-loop controlled chemical apparatus 200 has numerous advantageous and unexpected benefits and uses. In an embodiment, a process for performing closed-loop control of closed-loop controlled chemical apparatus 200 includes: producing, by analyte sensor 202, target voltage 205; contacting analyte sensor 202 and reference sensor 207 with composition 208; electrically perturbing, by analyte 204 in composition 208, analyte sensor 202; changing, in response to the electrical perturbation, voltage signal 203 from target voltage 205; receiving, by reference sensor 207, feedback control signal 209 from feedback controller 210; actively nulling, by reference sensor 207, the difference between the voltage signal 203 and the target voltage 205 when analyte sensor 202 is electrically perturbed by analyte 204 to maintain analyte sensor 202 at target voltage 205 for suppression of electrical noise fluctuations in closed-loop controlled chemical apparatus 200 that affect voltage signal 203; receiving, by gate terminal 212 of transistor 211, gate potential 214 such that drain current 215 of transistor 211 is maintained at the constant value in response to receipt of feedback control signal 209 by reference sensor 207, wherein transistor 211 is operated at an optimal transduction condition comprising peak sensitivity of transistor 211 and minimum noise of transistor 211 based on reference sensor 207; receiving, by feedback controller 210, transduction signal 216; determining setpoint 217 from transfer characteristics of transistor 211; determining, by feedback controller 210, the deviation of transduction signal 216 from setpoint 217; producing, by feedback controller 210, feedback control signal 209 that minimizes the deviation of transduction signal 216 from setpoint 217 based on control model 218; and communicating feedback control signal 209 from feedback controller 210 to reference sensor 207 and suppressing the electrical noise fluctuations to perform closed-loop control of closed-loop controlled chemical apparatus 200.

The process also can include receiving, by input terminal 219 of phase-sensitive detector 213 that is in electrical communication with drain terminal 221 of transistor 211, drain current 215 from drain terminal 221; communicating, by output terminal 220 of phase-sensitive detector 213 that is in electrical communication with source terminal 222 of transistor 211, oscillating voltage 223 to source terminal 222; comparing, by phase-sensitive detector 213, drain current 215 to oscillating voltage 223; producing, by phase-sensitive detector 213, direct current signal 224 that is proportional to a phase difference between drain current 215 and oscillating voltage 223; and communicating direct current signal 224 to feedback controller 210 as transduction signal 216.

The process can include receiving, by summer 225 in electrical communication with analyte sensor 202, feedback controller 210, and gate terminal 212, feedback control signal 209 from feedback controller 210; receiving, by summer 225, voltage signal 203 from analyte sensor 202; summing, by summer 225, feedback control signal 209 and voltage signal 203 to produce gate potential 214; and communicating gate potential 214 from summer 225 to gate terminal 212.

Closed-loop controlled chemical apparatus 200 and processes disclosed herein have numerous beneficial uses, including linearizing the response of closed-loop controller chemical apparatus 200, maintaining the transducer 229 at its optimal operating point for high-resolution measurements, tuning the dynamic range of the measurement in some embodiments, and actively suppressing the measurement noise using the feedback controller 210. Advantageously, closed-loop controlled chemical apparatus 200 overcomes limitations of technical deficiencies of conventional compositions such as highly nonlinear sensor response, high flicker noise at measurement bandwidths of interest, and non-uniform measurement resolution across the sensor dynamic range. Further, closed-loop chemical apparatus 200 overcomes limitations of conventional compositions through the composition of the compound sensor, transducer and feedback controller.

Closed-loop controlled chemical apparatus 200 and processes herein unexpectedly transforms the sensor response to provide consistently low noise operation across all of the dynamic range, provides a linear sensor response, and drastically improves measurement resolution through active noise suppression. Moreover, closed-loop controlled chemical apparatus 200 provides integrated sensors for chemical sensing of liquid or gas to sense analytes of interest.

The articles and processes herein are illustrated further by the following Example, which is non-limiting.

EXAMPLE

Rapid, quantitative therapeutic screening for Alzheimer's enzymes enabled by optimal signal transduction with transistors.

Field-effect transistors (FETs) have a long history as sensitive and label-free bioanalytical tools. Since that time FETs have been adapted for numerous applications ranging from measurements of protein-ligand interactions, monitoring of ocean acidification, low-cost DNA sequencing, enzyme measurements, and the detection of ionic action potentials in nerve and other neuronal systems. FET sensors are fabricated using nanomanufacturing processes that leverage silicon-based complementary metal-oxide semi-conductor (CMOS) technology. More recently, the emergence of 2D semi-conducting materials has resulted in new FET-based chemical sensors, and novel device geometries such as dual-gate FETs, which provide ≈100-fold higher sensitivity than silicon devices, while simultaneously improving the signal-to-noise ratio (SNR) of the measurements.

The sensitivity and resolution of pH measurements are metrics of device function and are used, in particular, to validate the performance of new FET structures and designs. Conventional ISFET technology has been optimized to return a pH sensitivity that approaches the Nernst potential of 59.5 mV per unit change in pH at room temperature. Efforts to improve the sensitivity of pH measurements have led to the exploration of dual-gate FETs, which leverage the asymmetric capacitive coupling between the top- and back-gate with the device channel to amplify small pH signals. Using this approach, recent measurements have demonstrated the amplification of pH signals by 2-fold with silicon devices and 37-fold (2.25 V/pH) to 75-fold (4.4 V/pH) higher than the Nernst value using novel channel materials and gate structures. However, the improvement in sensitivity does not always result in better pH resolution for silicon devices. As a result, the pH resolution of silicon ISFETs range from $50\times10^{-3}$ for commercial ion sensitive field-effect transistors (ISFETs) to as low as $10\times10^{-3}$ for silicon nanowire devices. On the other hand, dual-gate FETs fabricated with a 2D $MoS_2$ channel and with a room temperature ionic liquid top-gate dielectric have been demonstrated with a pH resolution as small as $92\times10^{-6}$ at a bandwidth of 10 Hz. In particular, the devices, which were operated in a low-noise regime of the atomically thin channel, exhibit a linear scaling in pH resolution improvement with device gain.

In order to drive adoption of high-resolution FET measurements within bioanalytical applications, we show how techniques developed for dual-gate FETs can be applied to commercially sourced silicon FETs. The techniques allow silicon devices to achieve pH readout resolution that exceeds most ISFET results and is on par with a solid-state version of recently published dual-gate 2D FETs (dg2DFETs). Improved performance of both nFETs and dg2DFETs was achieved in a remote sensing configuration where the pH sensitive surface is located off-chip and connected electrically to the FETs. The advantage of the remote sensing approach is that the signal transduction is separated from sensing, allowing reuse of the electronic components and minimizing parasitic noise sources. This setup differs from ISFET studies where the gate dielectric also serves as the pH sensing membrane.

This Example shows high-resolution pH measurements by comparing closed-loop transduction using an nFET to the open-loop operation of the same device. The improved performance establishes that this approach can allow use of transistors for laboratory grade bioanalytical measurements. Furthermore, the closed-loop transduction approach can be applied to a wide range of sensor technologies that could be based on other stand-alone transistors such as junction FETs (JFETs) and bipolar junction transistors (BJTs) and even to integrated sensors such as ISFETs. This readout approach improves performance of sensor systems based on any of these transistors. The technique is demonstrated through measurements of the activity and the effect of customized polypeptide therapeutics on the kinase Cdk5, which is implicated Alzheimer's disease and numerous other debilitating disorders.

With regard to n-channel silicon field-effect transistors, silicon field-effect transistors (nFETs) were soldered onto a printed circuit board (PCB) prior to measurements using a commercial probe station. Electrical characterization of the nFETs was performed using a semiconductor parameter analyzer. Time-series measurements with the nFETs were performed similar to the dg2DFET measurements as described below.

With regard to 2D dual-gate transistor fabrication, monolayer $MoS_2$ was first transferred onto an oxidized Si substrate ($SiO_2$) with a thickness of 70 nm using the gold-mediated exfoliation technique. The thickness of the transferred material was confirmed with Raman spectroscopy. Optical lithography was used to first pattern the source (S) and drain (D) contacts followed by electron-beam metal deposition (80 nm Au on 2 nm Ti) and lift-off in acetone. We then used a second optical lithography step to define and etch a 5 μm×5 μm channel for each FET. The devices were then annealed under forming gas (5% H2, 95% Ar) for 24 hours to minimize organic contamination and improve the contact resistance. This step was followed by the atomic layer deposition (ALD) of a 20 nm top-gate (TG) $Al_2O_3$ dielectric. Finally, another optical lithography step was used to pattern the top-gate metal, followed by electron-beam metal deposition (100 nm Au on 10 nm Ti) and lift-off in acetone.

With regard to remote biological activity measurements, the enzyme and pH calibration measurements using the dg2DFETs and nFETs were performed by connecting a pH sensor to the top-gate metal contact using a shielded coaxial cable. This allowed electronic components to be separated from the biological components and thereby reused. In the present work, a glass combination microelectrode capable of measurement volumes as small as 50 μL was used as the pH sensor, although the techniques described here are compatible with other sensing and bioanalytical surfaces that can be electrically connected to the top-gate metal contact.

With regard to time-series field-effect transistor measurements and PID control, time-series measurements were performed by operating the nFETs and dg2DFETs under proportional-integral-derivative (PID) control. The channel current, $I_D$, was maintained at a constant value by continuously varying the back-gate voltage ($V_{BG}$) in the case of the dg2DFETs (FIG. 8a) or by adding the controller output to the signal from the pH sensor ($V_{pH}$) for the nFETs (FIG. 9c) in response to changes in the top-gate potential.

The PID control system was implemented by first amplifying the channel current, $I_D$, using a current preamplifier (DLPCA-200; FEMTO, Berlin, Germany) using a gain of either $10^6$ V/A (dg2DFET) or $10^3$ V/A (nFET). The output of the current preamplifier was then filtered using a 4-pole Bessel filter with a cutoff frequency of 5 kHz and sampled with a frequency of 25 kHz using a 14-bit analog-to-digital converter. The digital PID controller ($K_P$=553.5 mV, $K_I$=9.22×$10^3$ $s^{-1}$ and $K_D$=10.4 μs) was operated with a bandwidth of 1 kHz to maintain the channel current setpoint. Because most biological processes are slow and do not require high bandwidth measurements, the controller output was further filtered using a low-pass filter with a cutoff frequency of 10 Hz prior to being recorded.

With regard to sensitivity and resolution of pH measurements, the pH sensitivity and resolution were established, wherein a histogram from the raw $V_{PID}$ time-series data was computed for each measured pH. A sum of two Gaussian distribution functions was then fit to the histograms to obtain the peak positions and standard deviations of the reference potential and the measured pH signal. The difference in the peak positions between the pH and reference potentials ($\Delta V_{PID}$) was used to determine the pH sensitivity of the device. The measurement uncertainty ($\sigma_{PID}$) was then obtained by propagating the error when determining $\Delta V_{PID}$. For the nFETs, the pH resolution, $\Delta pH=(k \times \sigma_{PID})/V_{Nernst}$ is reported with expanded uncertainty (k=2), where $V_{Nernst}$ is the Nernst potential at room temperature. For the dg2DFETs, $\Delta pH=k\sigma_{PID}/(\alpha \times V_{Nernst})$, where α is the device gain.

With regard to kinase measurement reagents, the activity of Cdk5/p25 was estimated by measuring the phosphorylation of histone H1. All measurements were performed with 18.5 nM of Cdk5/p25 in 1× kinase buffer to match physiological conditions using a volume of 50 μL. The substrate protein histone H1 was suspended in deionized water at a stock concentration of 2 mg/mL and further diluted as described in the in the Results section. Substrate phosphorylation was initiated with a mixture of dithiothreitol (DTT) and adenosine triphosphate (ATP) with final concentrations of 250 μM and 5 mM respectively. The measurements were buffered using 5× kinase buffer, prepared by suspending 25 mM β-glycerol, 50 mM $MgCl_2$, 5 mM EGTA, 2.4 mM EDTA, 1.25 mM MOPS in deionized water (DIW) and diluting further to form 1× kinase buffer.

We electrically characterized nFET and dg2DFET devices to evaluate their performance and to determine the optimal operating conditions for biosensing applications. The devices were calibrated with standard pH buffer solutions to determine the gain, α, of the dg2DFET, noise performance, sensitivity, and resolution. Finally, both device types were used to measure the activity of the kinase Cdk5, an enzyme implicated in Alzheimer's disease and to evaluate the effectiveness of a custom polypeptide, p5, as a therapeutic agent in modulating Cdk5 function.

Figure 6:
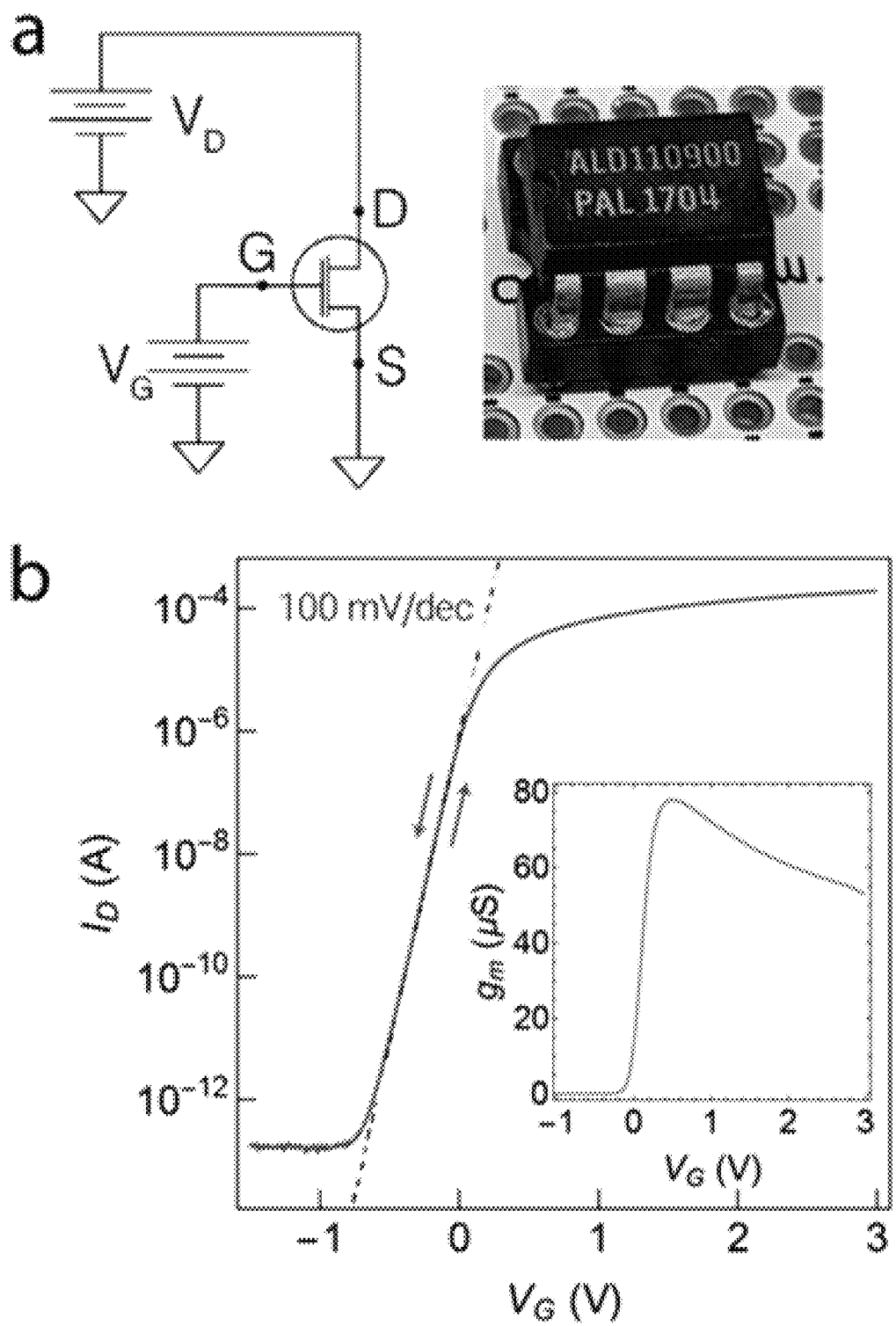
FIG. 6 shows an electrical characterization of an n-channel field-effect transistor (nFET) for biosensing. (a) left: Schematic of the electrical characterization setup of the nFET. A constant voltage, $V_D$, is applied to the drain contact while the source is grounded. The transfer characteristics of the device are obtained by sweeping the top-gate voltage, $V_G$, to electrostatically control the channel current ($I_D$). right: An image of the packaged nFET used in this work. (b) The transfer curve of the nFET is shown by measuring $I_D$ as a function of a sweep of $V_G$. (inset) The device transconductance as a function of $V_G$. The voltage at peak transconductance determines the point of maximum sensitivity and is used to optimally bias the device for biosensing.

Silicon n-Channel FET Performance. The nFETs (FIG. 6a; right) were first characterized electrically using the configuration shown in the schematic in FIG. 6a (left). The transfer characteristics of the device were determined by recording the drain current ($I_D$) as a function of the gate potential ($V_G$), while the drain voltage ($V_D$) was held constant. FIG. 6b shows the typical transfer characteristics ($I_D$-$V_G$) for the nFETs. The device exhibits up to orders of magnitude change in $I_D$ when switching from an off-state to an on-state with a steep sub-threshold slope of ≈100 mV/dec at ≈300 K and gate leakage current ($I_G$) was ≈1 pA. FIG. 6 (inset) shows the transconductance ($g_m$), obtained by taking the numerical derivative of the transfer curve. The peak transconductance of the nFETs ($g_{m,peak}$) was found to be 78.1 µS at a voltage ($V_{gm,max}$) of 0.385 V.

Figure 7:
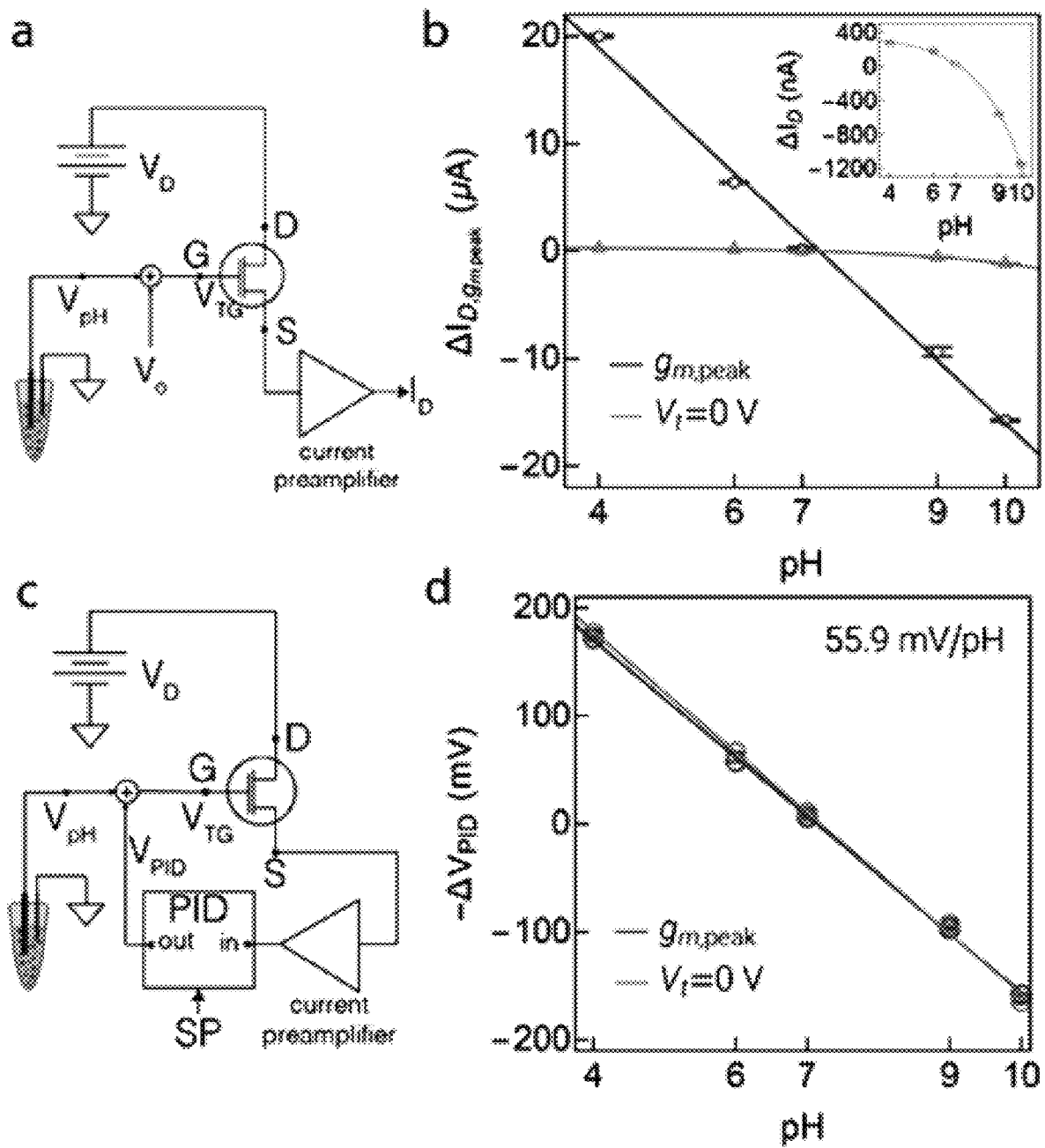
FIG. 7 shows calibration of pH using a commercially sourced n-channel silicon field-effect transistor (nFET). The error bars in all cases represent the expanded uncertainty (k=2) of the measurand. (a) The nFET was operated in open-loop by directly measuring the changes in the drain current ($I_D$) due to changes in the gate potential ($V_{TG}$) applied to the top-gate contact (G). A constant offset potential ($V_o$) was summed with the potential ($V_{pH}$) generated by a glass pH microelectrode prior to being applied to the gate contact. (b) The change in $I_D$ as a function of measuring standard pH buffer solutions ranging from pH 4 to pH 10 using a glass pH microelectrode. Setting $V_o$ to operate the device at peak transconductance ($g_{m,peak}$) resulted in a linear response over the measured pH range. Operating the device about the threshold voltage ($V_T$) of 0 V resulted in a highly non-linear pH response (inset). (c) Constant current mode operation of the FET was performed by using a proportional-integral-derivative (PID) controller to monitor $I_D$ and continually adjust the PID voltage ($V_{PID}$). $V_{PID}$ was summed with $V_{pH}$ prior to being applied to the gate contact. (d) The change in $V_{PID}$ as a function of measuring standard pH buffer solutions ranging from pH 4 to pH 10 using a glass pH microelectrode. The PID set-point was set to a value of $I_D$ to allow device operation either at $g_{m,peak}$ or at the threshold voltage of 0 V.

With regard to pH sensitivity using n-channel silicon transistors, the pH sensitivity of the nFETs was measured using commercial standard pH buffer solutions over a range of 4 to 10. When operating the device in open-loop (FIG. 7a), we found the pH response to be linear when the device was operated about $g_{m,peak}$ as seen in FIG. 7b. This behavior is expected when operating the device in the linear regime of the transfer curve (see FIG. 6). Under these conditions, we found the pH sensitivity, $\delta I_D/\delta pH \approx 6$ µA ($R^2=0.992$) when $V_D=0.1$ V, yielding a transimpedance gain of $9.9\times10^3$ V/A, assuming $V_{Nernst}$ of 59.5 mV at room temperature (300 K). The pH response was drastically different, as expected, when the device was operated about its threshold voltage ($V_T=0$ V). In this case, the pH response was linear under acidic conditions (pH<7), when the pH sensor returned a positive potential, thereby driving the FET into the inversion regime. On the other hand, under more basic conditions (pH>7), the sensor potential was negative causing the nFET to operate in the sub-threshold regime where the current decreases exponentially at negative gate potential. The net result is a pH response that is highly non-linear over the measured pH range. Therefore, it can be advantageous to operate the nFET in the linear regime, particularly when operating over a wide pH range. Additionally, the larger $I_D$ in the linear regime over its value at $V_T$ results in lower relative noise and improved pH resolution as discussed in greater detail in later sections.

The sensitivity and performance of the commercial nFET improved considerably when operated under closed-loop PID control as shown schematically in FIG. 7c. In this configuration, the controller continually adds a control voltage ($V_{PID}$) to $V_{pH}$, thereby maintaining $I_D$ at a constant value. A key advantage of this approach is that because the device will always operate at the same point in its transfer curve (see FIG. 6b), its performance remains consistent across a wide range of measured pH values. This is clearly seen in FIG. 7d, where the device exhibits a linear pH response ($R^2=0.997$) both when the PID controller was set up to hold the nFET at $g_{m,peak}$ (FIG. 7d) and when the device was operating at its $V_T$ of 0 V (FIG. 7d). Furthermore, the pH sensitivity of the system in both cases, obtained from a linear regression of the curves in FIG. 8d, was found to be ≈56 mV per unit change in pH, approaching the Nernst value of 59.5 mV per unit change in pH at room temperature. Finally, the separated gate configuration of the system setup allows the PID output to be summed with the sensor signal, allows the controller to operate at higher bandwidths and enables better suppression of noise, thereby improving pH resolution.

Figure 8:
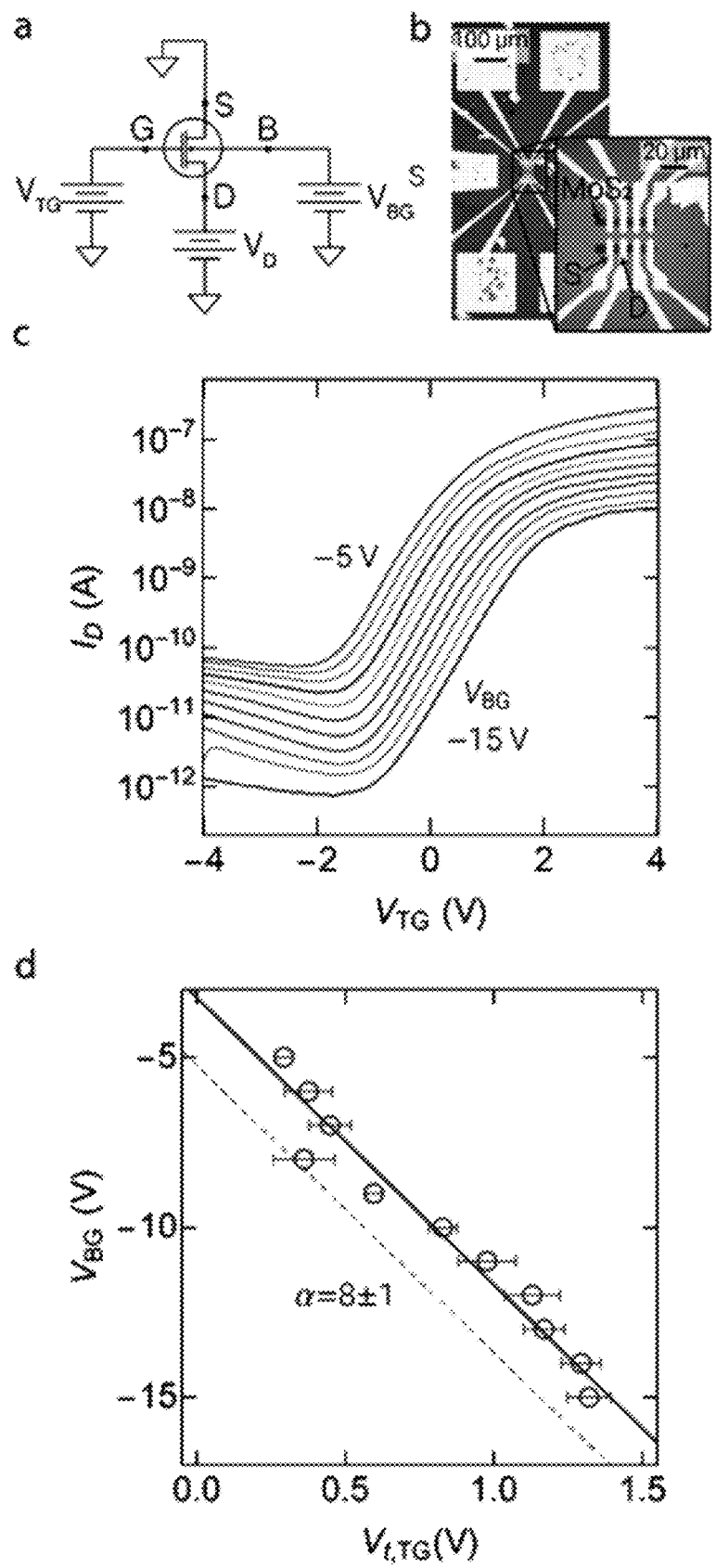
FIG. 8 shows electrical characterization of dual-gated monolayer $MoS_2$ FET for biological sensing applications. (a) Measurement schematic for characterizing a dual-gated 2DFET for remote biosensing. The $MoS_2$ 2D semi-conducting channel spans the source (S) and drain (D) contacts. While the source contact is grounded, a constant potential ($V_D$) is applied to the drain contact driving a current across the 2D channel. Channel conduction is electrostatically controlled by a voltage applied to the silicon substrate, which forms the global back-gate (B) or to the metal top-gate (G). (b) Top view optical image of an array of 2D $MoS_2$ FETs. (c) Transfer characteristics of a dual-gated 2D FET showing drain current ($I_D$) as function of the top-gate voltage ($V_{TG}$) while stepping back-gate voltage ($V_{BG}$). (d) The change in $V_{BG}$ as function of top-gate threshold voltage ($V_{t,TG}$) is shown. A linear regression to the data (n=5) is used to determine the signal amplification ($\alpha$) of $V_{TG}$ at the back-gate. The error bars report the standard error defined as the standard deviation of the population mean.

Dual-Gate 2D FET Performance. We compared the performance of the nFETs with the dg2DFETs that we fabricated using atomically thin $MoS_2$ films. An optical image of a representative dg2DFET device is shown in FIG. 8a (right). The dg2DFETs were electrically characterized following fabrication using the setup shown schematically in FIG. 8a (left). The transfer characteristics of the device were measured by recording the drain current ($I_D$) as a function of the top-gate potential ($V_{TG}$) with the drain voltage ($V_D$) held constant. The measurements were repeated for different $V_{BG}$ to determine the signal amplification (a) due to the asymmetric capacitance of the top and back gates (FIG. 8b).[8] The devices exhibited a dynamic range of up to orders of magnitude in $I_D$ and a subthreshold slope consistent with expected behavior for a 20 nm high-k gate dielectric.

For each curve in FIG. 8b, the top-gate threshold voltage ($V_{t,LG}$) was determined from a linear extrapolation of the peak transconductance to the x-axis. FIG. 7c plots the back-gate voltage ($V_{BG}$) against the top-gate threshold voltage ($V_{t,TG}$). This allowed the determination of the device gain using the expression $\alpha=dV_{BG}/dV_{t,TG}$. The value of α for devices measured as part of this work was then determined numerically from a linear regression to the data in FIG. 6c, resulting in $\alpha=8\pm1$, or times larger than conventional dual-gate silicon devices. The measured value of α is in good agreement with theoretical predictions for devices with a 20 nm $Al_2O_3$ top-gate dielectric and 70 nm $SiO_2$ bottom oxide.

The dg2DFETs presented here do not operate in the quantum capacitance limited regime. This is due to the fact that, in the inversion regime where the dg2DFETs operate, the top- and back-gate capacitances ($C_{TG}\approx0.4$ µF/cm$^2$ and $C_{BG}\approx0.05$ µF/cm$^2$) are more than an order of magnitude smaller than the quantum capacitance ($C_Q\approx4$ µF/cm$^2$) of the 2D channel. This allows us to ignore the effects of $C_Q$, giving rise to the simplified expression for the device gain, $\alpha=dV_{BG}/dV_{t,LG}=C_{TG}/C_{BG}$.

With regard to a pH sensitivity of dual-gate 2D FETs, the dg2DFETs were operated in a constant current mode shown in FIG. 9a. A PID controller was used to maintain $I_D$ at a preset value by continuously varying $V_{BG}$ in response to changes in $V_{TG}$. The controller current set-point (50 nA) and a DC offset voltage applied to the top gate ($V_o$=+0.5 V) were optimized to operate the device in the linear and low-noise region of the transconductance curve as determined from FIG. 8c. The performance of the device was then validated by applying a sine wave at a frequency of 1 Hz and peak-to-peak amplitude of 200 mV to the top-gate and measuring the response of $V_{BG}$ (FIG. 9b) as regulated by the PID controller. The device gain, a, was then obtained from the ratio of the amplitudes of $V_{BG}$ to $V_{TG}$ to yield $\alpha=5.8\pm0.1$, consistent with the value obtained from the data in FIG. 7c.

Figure 9:
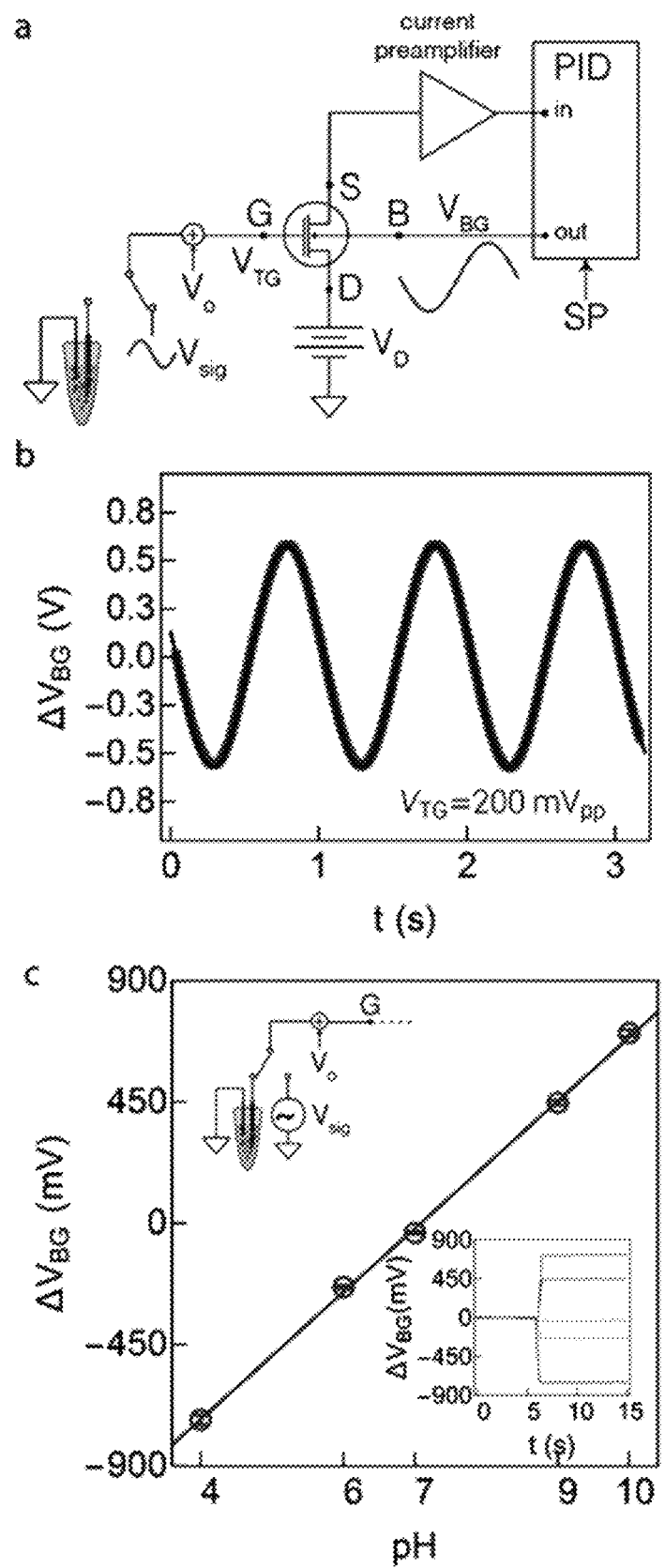
FIG. 9 shows electrical calibration and pH sensitivity measurements of dual-gate 2D field-effect transistors (dg2DFETs) when operated in a constant current mode. (a) Schematic representation of constant current mode operation of dg2DFETs.[8] A proportional-integral-derivative (PID) controller was used to maintain the channel current ($I_D$) at a constant value. Control of $I_D$ was achieved by continually adjusting the back-gate voltage ($V_{BG}$) in response to changes in the top-gate potential ($V_{TG}$) applied either using a waveform generator or from the output of a pH sensor ($V_{sig}$). A DC offset voltage ($V_o$) was summed with $V_{sig}$ to determine the optimal operation region of the dg2DFET. (b) The time-variant response of $V_{BG}$ under PID control is shown when the top-gate is biased with a 1 Hz AC sine wave signal with a peak-to-peak amplitude of 200 mV. (c) Response of $V_{BG}$ when measuring standard buffer solutions from pH 4 to 10. The error bars represent the expanded uncertainty (k=2) of the measurement. (inset) Time-series data, relative to a reference potential value, show the response of $V_{BG}$ when measuring standard buffer solutions from pH 4 to 10.

The pH sensitivity of the dg2DFETs was measured by remotely connecting a pH sensor to the top-gate metal contact using a shielded cable. A switch was used to alternatively either ground the top-gate or connect it to the pH sensor. Time-series measurements of the system response, under PID control, to commercial standard buffer solutions from pH 4 to pH 10 are shown in FIG. 9. 4d (inset). The time-series data were analyzed to yield the pH response curve in FIG. 9c with a sensitivity, $\delta V_{BG}/\delta pH=236.3$ mV ($R^2=0.998$).

Figure 10:
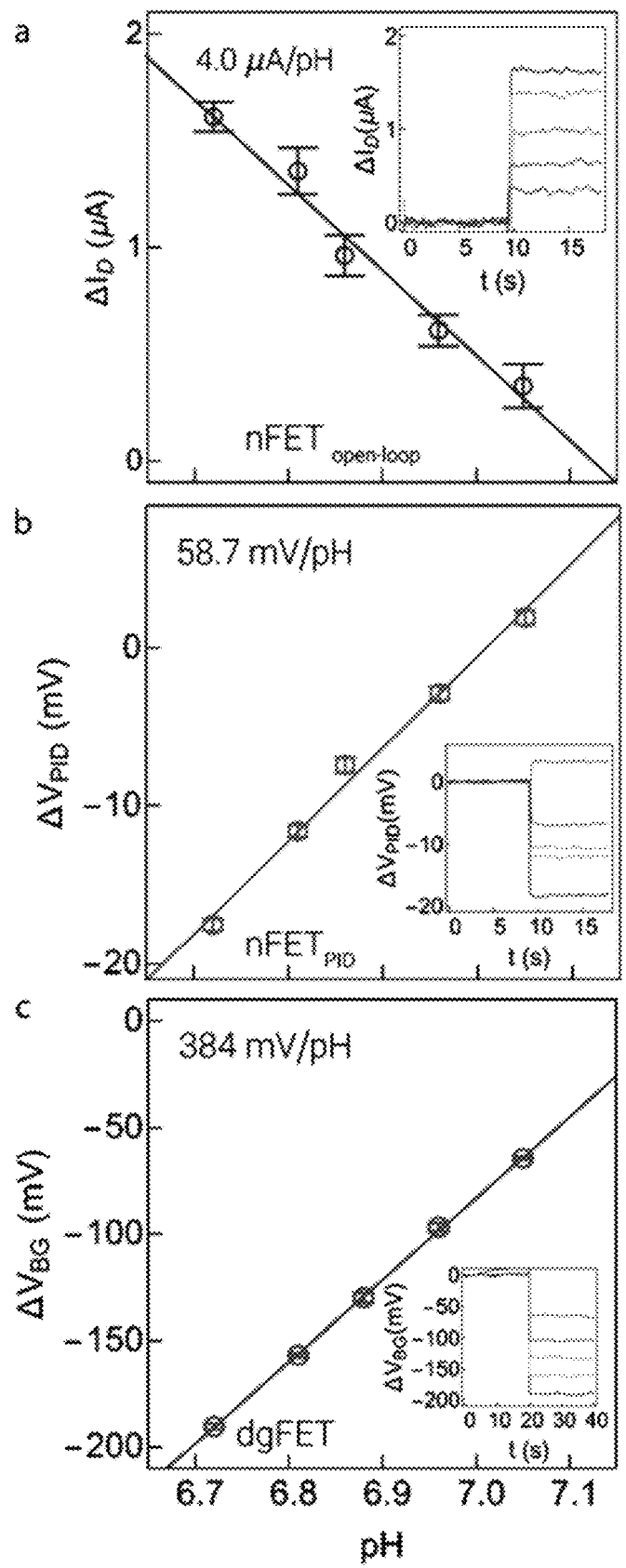
FIG. 10 shows a comparison of pH sensitivity and resolution between a commercially sourced n-channel silicon field-effect transistor (nFET) and a 2D dual-gated $MoS_2$ transistor (dg2DFET) operating under closed-loop proportional-integral-derivative (PID) control when measured using a glass microelectrode. The error bars in all cases represent the expanded uncertainty (k=2) of the measured quantity shown on the y-axis of the plot. (a) The change in the nFET channel current ($\Delta I_D$) when operating the device in open-loop, as a function of phosphate buffered saline (PBS) solutions adjusted to different pH values. (b) The change in the PID control voltage ($\Delta V_{PID}$) as a function of solution pH when operating the nFET devices with PID control. (c) The change in $\Delta V_{PID}$ as a function of solution pH when operating dg2DFETs under PID control. (insets) Underlying time-series data from nFETs and dg2DFETs that were analyzed to obtain the plots in panels (a), (b) and (c)

With regard to pH resolution of n-channel silicon and dual-gate $MoS_2$ transistors, pH resolution (0.4 pH) of nFETs and dg2DFETs at a bandwidth of 10 Hz were determined when measuring phosphate buffered saline (PBS) and are summarized in FIG. 11. Following a procedure in which a switch alternatively connected the gate terminal to the PBS solution or to ground. This method allowed the measurements of time-series of nFETs operated in an open-loop as seen in FIG. 10a. A histogram of the time-series was then used to determine the mean value of $I_D$ for each measured pH solution and the expanded uncertainty (k=2). As seen from FIG. 10a, a linear regression of the measured pH data yielded a sensitivity, $\delta I_D/\delta pH \approx 4$ µA ($R^2=0.974$) when $V_D=0.1$ V, similar to the value obtained from the data in FIG. 9b. By inverting the curve in FIG. 9b and propagating the uncertainty in $I_D$, we determined $\Delta pH$ with an expanded uncertainty (k=2) to be $(22\pm2)\times10^{-3}$ at a bandwidth of 10 Hz in the open-loop configuration.

The measurements were repeated when operating the nFET under PID control as seen from FIG. 8c. The time-series of the PID controller output (FIG. 10b, inset) were analyzed identically to the open-loop data to yield a pH sensitivity, $\delta V_{BG}/\delta pH=58.7$ mV ($R^2=0.988$) as seen from FIG. 10b, consistent with the expected value of $V_{Nernst}$ at room temperature. The error bars at each measured pH value, which represent the expanded uncertainty (k=2) in the PID output voltage, are a direct measure of ΔpH. We found that, on average, $\Delta pH=(7.2\pm0.3)\times10^{-3}$ at a bandwidth of 10 Hz or an improved over nFETs operating in open-loop.

Both modes of nFET operation described above were compared with pH measurements performed using dg2DFETs. FIG. 10c (inset) shows time-series measurements of pH sensitivity of PBS buffers using dg2DFETs when they were operated using PID control as described previously in FIG. 8a. An analysis of the pH time-series (see Experimental section for details) yielded sensitivity, $\delta V_{BG}/\delta pH=384$ mV ($R^2=0.999$) as seen from FIG. 10c, which represents an ≈6.5-fold amplification of $V_{Nernst}$ at room temperature. The error bars in the figure estimate the expanded uncertainty (k=2) of the $\Delta V_{BG}$ at each pH value. This in turn allowed the estimation of the pH resolution using the expression $\Delta pH=\Delta V_{BG}/(\alpha\times V_{Nernst})=(3.9\pm0.7)\times 10^{-3}$ at a bandwidth of 10 Hz, or ≈2-fold better than the nFET devices operating under PID control.

Figure 12:
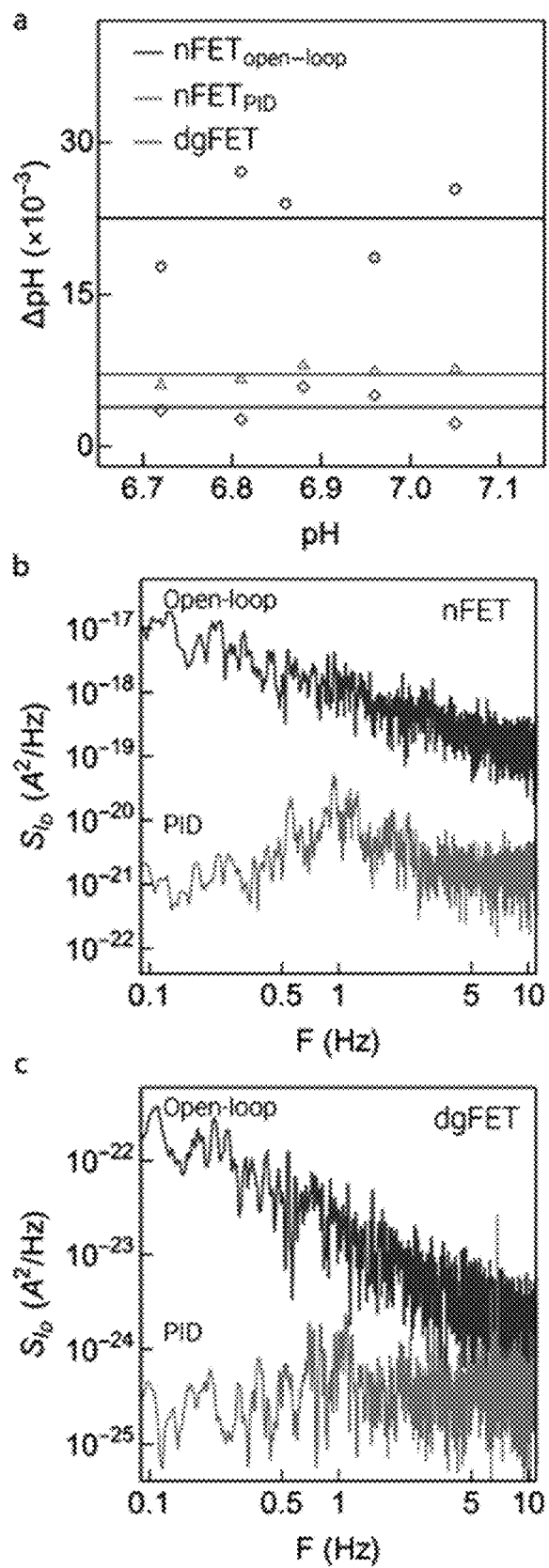
FIG. 12 shows (a) a comparison of the pH resolution ($\Delta pH$) as a function of pH when operating the n-channel silicon field-effect transistor (nFET) in open-loop, the nFET under PID control and the 2D dual-gated $MoS_2$ transistor (dg2DFET) under PID control. (b) Power spectral density (PSD) of the channel current, $I_D$, of nFETs under open-loop operation and under PID control. (c) Power spectral density (PSD) of the channel current, $I_D$, of dg2DFETs s under open-loop operation and under PID control.

As seen from FIG. 12a and FIG. 11, the pH resolution of nFETs can be substantially improved by operating them under PID control. Under this mode of operation, the low intrinsic noise and the high channel currents of the nFETs allow their performance to approach that of custom-built dg2DFETs (FIG. 12a). To better understand the improvement in nFET performance under PID control, we measured the power spectral density (PSD) of the channel current noise, $S_{ID}$, as seen in FIG. 12b. Under open-loop operation (FIG. 12b), the devices exhibit 1/f noise scaling as observed by others in the literature.[15,25] The root mean squared (RMS) noise in the channel current ($\delta I_D$) was then determined using the expression $\sqrt{\int_{BW} S_{ID} df}$ to be 2.5 nA in the open-loop case for a bandwidth of 10 Hz. The PID controller greatly suppresses 1/f noise as seen from FIG. 12b, pink. When operating under PID control, we found $\delta I_D$ to be 0.18 nA, or an order of magnitude lower for a bandwidth of 10 Hz, and directly results in the improved ΔpH seen in FIG. 12a.

An improvement in the channel current noise is also observed for the dg2DFETs when operating under PID control, in comparison with the open-loop case, as seen from FIG. 12c. At a bandwidth of 10 Hz, $\delta I_D$ decreased from 7.0 pA for open-loop operation to 2.1 pA when operating under PID control. However, in contrast to the nFETs, the dual-gate devices have an intrinsic gain of ≈6.5, which improves their overall performance. In order to directly compare the nFETs with dg2DFETs when both devices were operating under PID control, we determined the relative error for each case as $\delta I_D/I_D$, where the channel current, $I_D$, is also the current set-point for the PID controller. For the nFETs this value was 40.5 µA to coincide with $g_{m,peak}$, and 50 nA for the dg2DFETs. This results in $\delta I_D/I_D=4.3\times10^{-6}$ for the nFETs, and $\delta I_D/I_D=4.2\times10^{-5}$ for the dg2DFETs. The order of magnitude lower relative noise in the nFETs is offset by the gain, α, resulting from the dual-gated structure of the dg2DFETs as measured in FIG. 7 and is consistent with the measured improvement in ΔpH as seen in FIG. 12a (nFET$_{PID}$; and dg2DFET).

While the pH resolution of the nFETs can approach that of the dg2DFETs with a moderate internal gain, their performance is expected to fall short of high gain devices such as ionic liquid gated dual-gate FETs. The highly asymmetric gate geometries of the ionic liquid gated FETs allows the realization of α>150 while operating in a low-noise regime similar to the dg2DFETs. The combination of high gain and low noise allows those devices to resolve pH values as small as $92\times10^{-6}$, which is an order of magnitude below the resolution attainable by the dg2DFETs (FIG. 12a). While this improved resolution is useful in certain bioanalytical applications, we show below that the improvements in the operation modes of nFETs demonstrated here can be leveraged to measure both enzymatic activity and the effect of therapeutics on enzyme function at physiological concentrations.

With regard to Cdk5-p25 pathological activity and neurodegeneration, cyclin-dependent kinase 5 (Cdk5) is involved in neuronal development, memory, and pain signaling. Its physiological activators, the proteins p35 and p39, trigger the Cdk5-mediated phosphorylation of neuronal proteins and organelles that are essential for the normal function of the human nervous system. Factors, which include environment, lifestyle and genetics, result in an increased uptake of intracellular Ca' that activates the protease calpain, truncating p35 into the fragments p10 and p25. The latter is a pathological activator of Cdk5, leading to its hyperactivation. Multiple cascading effects within the cell cycle can be traced back to the hyperactivation of Cdk5 resulting in the formation of β-amyloid plaques and intracellular neurofibrillary tangles—the well-known indicators of neurodegenerative diseases such as Alzheimer's disease (AD).

Therapeutic approaches targeting Cdk5-related pathologies have focused on inhibitors such as Aminothizole and Roscovitine, which bind to the ATP-docking pocket and prevent Cdk5-mediated hyperphosphorylation. However, targeting the ATP-binding pocket also causes non-specific interactions with other ATP-mediated cellular reactions, often causing serious side-effects. This has led to the pursuit of alternative approaches, such as the use of cholinesterase inhibitors or antioxidants, which have thus far not resulted in safe therapeutics.

In past work, we have shown a novel approach to inhibit the Cdk5-p25 pathology, for example using the 24 amino acid, p5, obtained through the repeated truncation of p35. Importantly, these polypeptides act as selective inhibitors of Cdk5 pathological hyperactivity in both in vivo and in vitro experiments. A variant derived from p5, TFP5, which was designed to cross the blood-brain barrier showed a drastic decrease in pathology by allowing the rescue of cortical neurons in transgenic 5XFAD AD model mice in vivo.

We used computer simulations to determine the molecular basis of p5-based inhibition mechanisms—a step towards developing safe therapeutics for the regulation of Cdk5/p25 hyperactivity. This in turn could also lead to new molecules that are more selective and therefore safer. The FET-based measurements developed here can play a central role in this development cycle by enabling the rapid testing of candidate molecules. As a first step towards this goal, we demonstrate the ability of nFETs to measure the activity of Cdk5/p25 and the effect of p5 on re-regulation of this enzyme under physiological conditions.

Figure 13:
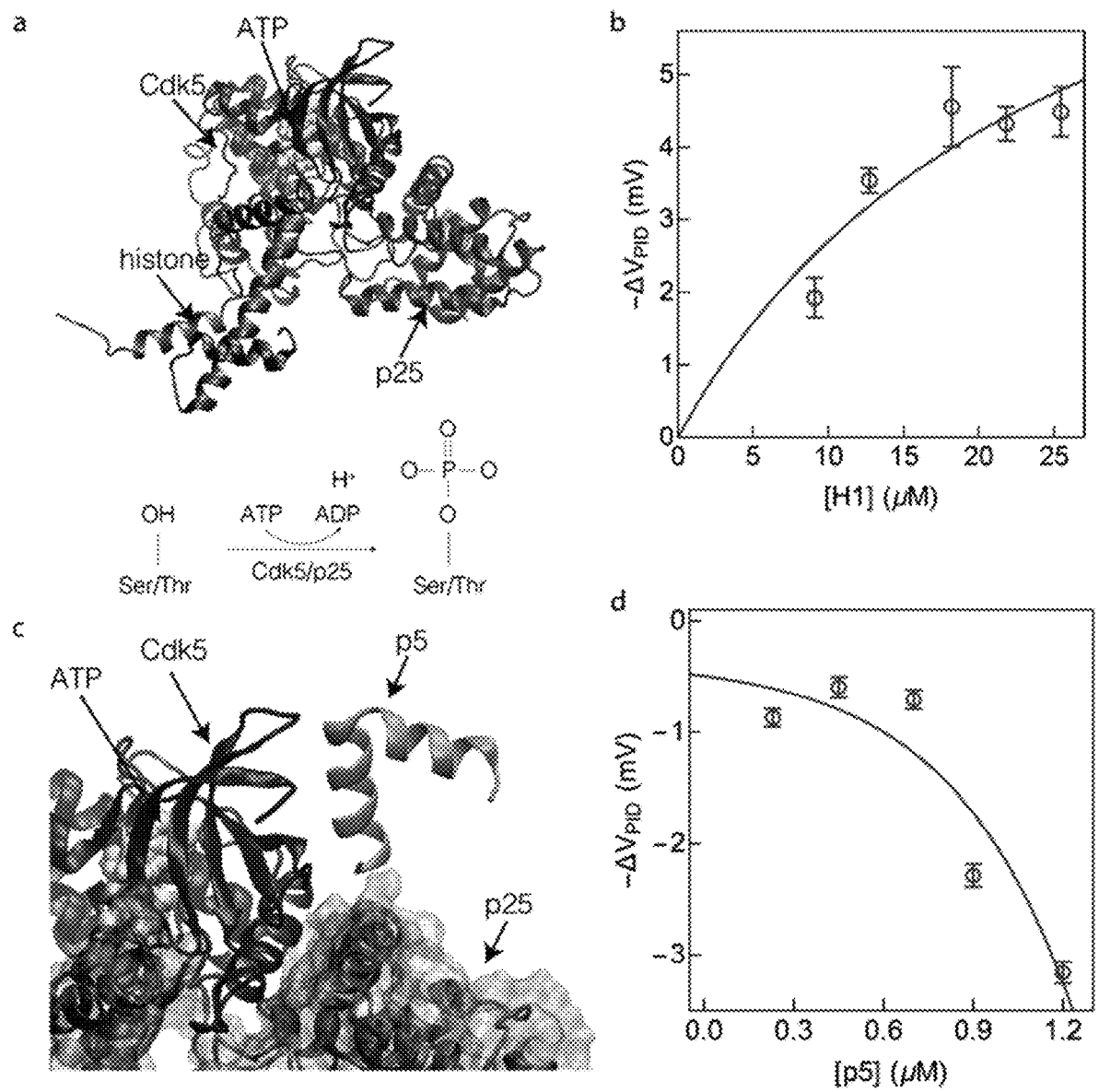
FIG. 13 shows measurements of the activity of the proline directed kinase, Cdk5 and the effect of the custom designed therapeutic polypeptide, p5, on modulating its activity. (a) (top) The molecular structure of the pathological Cdk5/p25 complex when phosphorylating a substrate protein, histone H1, during adenosine triphosphate (ATP) hydrolysis. (bottom) The reaction scheme of Cdk5-mediated phosphorylation of serine or threonine residues in histone. Upon hydrolysis of ATP, a single proton is released causing a slight acidification of the surrounding medium. (b) The change in the measured gate voltage ($\Delta V_{PID}$) of a n-channel silicon field-effect transistor (nFET) upon Cdk5-mediated phosphorylation as a function of the substrate protein, histone H1, concentration ([H1]). (c) Molecular representation of p5 interactions with the Cdk5/p25 complex that result in a decrease in its activity. (d) $\Delta V_{PID}$ as function of p5 concentration ([p5]) shows decreasing Cdk5 activity. The concentration of Cdk5/p25 and histone H1 were held a fixed value for each measurement in the plot. The error bars in (b) and (d) represent the expanded uncertainty (k=2) in $\Delta V_{PID}$.
Figure 14:
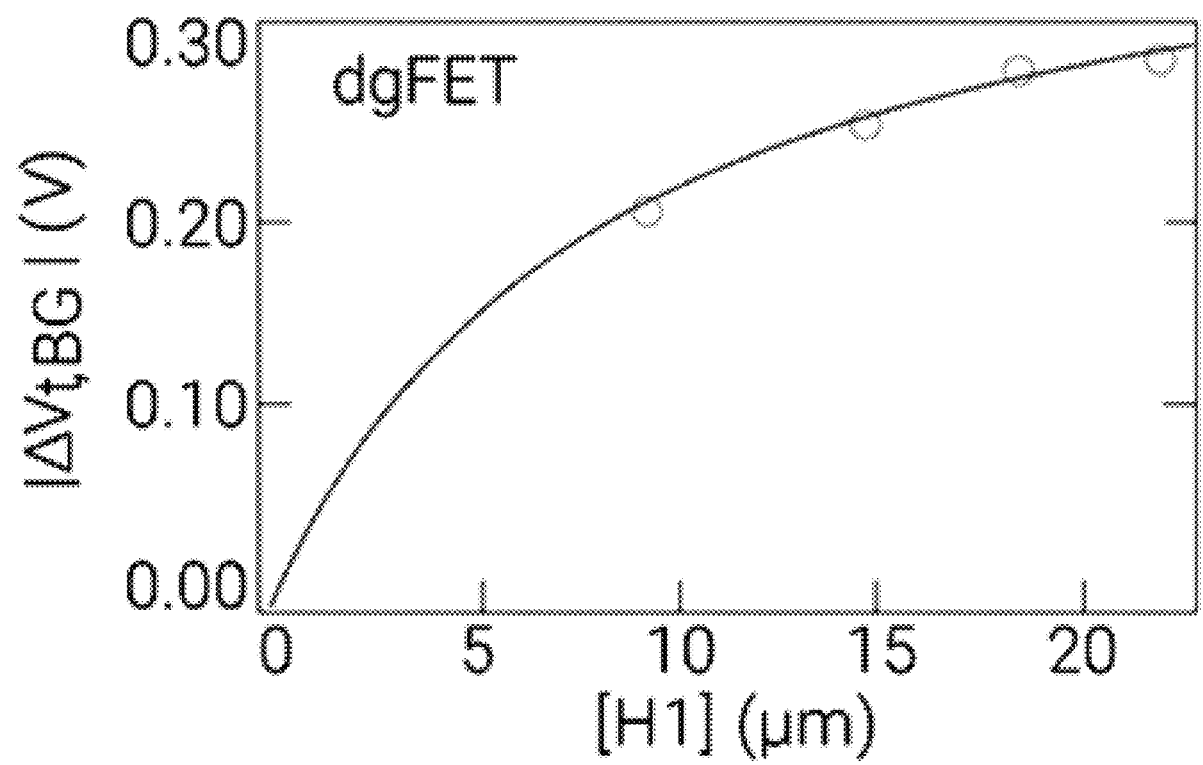
FIG. 14 shows steady-state measurements of Cdk5 activity using dual-gated field-effect transistors (dgFETs). The change in the solution pH was used as a reporter to detect and quantify enzyme-mediated phosphorylation of the protein histone H1. The change in the back-gate threshold ($V_{T,BG}$) as a function of histone H1 concentration ([H1]) showed a monotonic increase. A simple model was used to estimate the activity coefficient, $k_a$=(9.1±0.9) μM.
Figure 15:
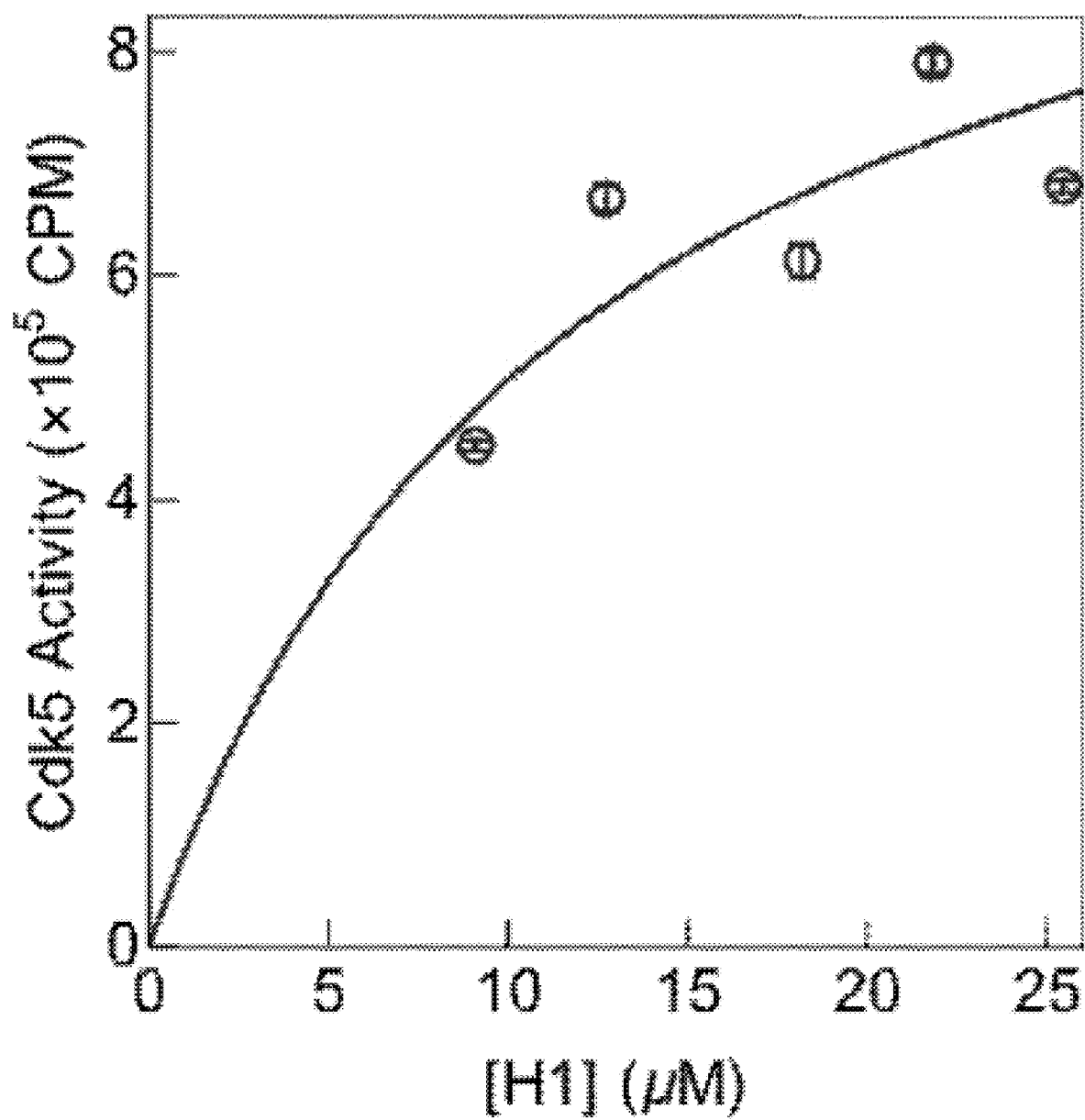
FIG. 15 shows activity of Cdk5/p25 that was determined using a radioactively labeled adenosine triphosphate ($\gamma$-$^{32}$P-ATP) assay as a function of the concentration of the protein histone ([H1]). A model was used to determine the activity coefficient, $k_a$=(12.1±2.3) μM. The error bars represent the standard deviation in Cdk5 activity.

Enzymatic Activity of the Pathological Cdk5-P25 Complex. FIG. 13a shows a molecular representation of the Cdk5-mediated phosphorylation (top) and the phosphorylation reaction scheme (bottom). In the presence of an activator protein (e.g., the pathological p25), Cdk5 catalyzes the transfer of a single phosphate group from ATP to a serine or threonine residue in a substrate protein (e.g., histone H1). The reaction also releases a single proton, thereby causing the surrounding medium to become slightly more acidic and decreasing its pH. When using the nFETs, the change in pH resulted in a change in $V_{PID}$, shown in FIG. 13b, relative to a control sample with no enzyme, for concentrations of histone ([H1]) ranging from 9 μM to 25 μM and is shown in FIG. 13b. All measurements were performed at a physiological concentration of Cdk5/p25 of 18.5 nM. As expected, the change in $V_{PID}$ increased monotonically with increasing histone concentration. A simple model of the form $$\gamma \frac{[H1]}{k_a + [H1]},$$

where $k_a$ is the activity of and γ is a scaling constant, was fit to the data in FIG. 13b. The value of $k_a$ was then estimated to be (8.2±1.3) μM when measured with the nFETs. This value was consistent with $k_a$=(9.1±0.9) μM for measurements performed using dg2DFETs (FIG. 14) under identical solution conditions, our previous measurements using a γ-$^{32}$P-ATP assay ($k_a$=12.1±2.3 μM) as seen from FIG. 15, and with literature values of Cdk5/p25 activity.[51] In each case, the error bars of the estimated quantity represent the standard error of the measurement.

Figure 16:
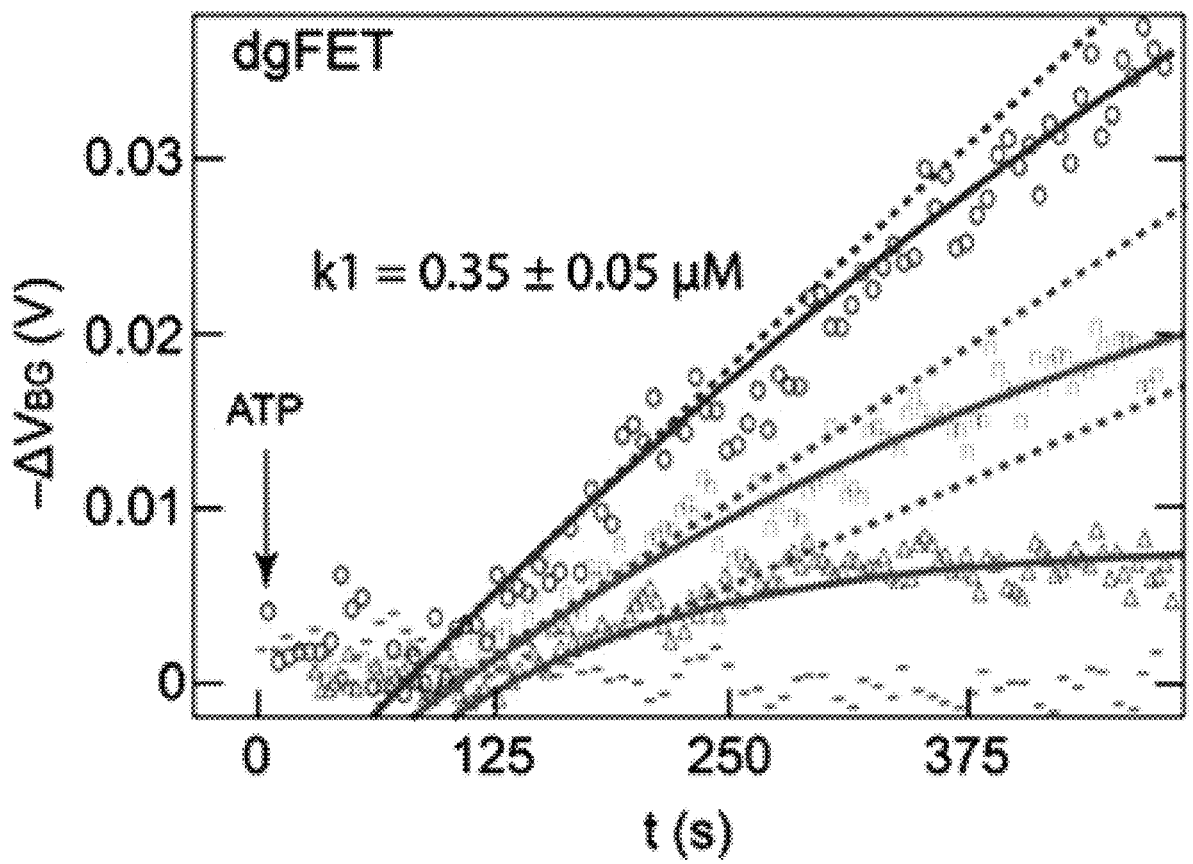
FIG. 16 shows a time-series measurements of enzyme catalyzed phosphorylation of histone H1 were measured with a dual-gated field-effect transistor (dgFET). The histone concentrations ([H1]) were 9.1 μM, 12.7 μM, 18.2 μM and a control sample with no histone. The solid lines depict a first order kinetics model that describes the time course of phosphorylation, while the dashed lines represent an estimate of the reaction velocity during the first 100 s after a change in the signal was detected.

We leveraged the high time-resolution of our technique to measure the kinetics of the Cdk5/p25 enzymatic reaction for histone concentrations of 9.1 μM, 12.7 μM and 18.2 μM as seen from FIG. 16. In each case, the reaction was initiated upon the addition of ATP. After minute, we observed a distinct change in the voltage signal that was indicative of histone phosphorylation. A control sample with no Cdk5/p25 showed no change in signal upon the addition of ATP. A nonlinear regression of the form $\beta(1-e^{-k_1 t})$, where β is a scaling constant, was used to estimate the enzyme rate constant $k_1$ to be (0.35±0.1) min$^{-1}$, consistent with literature values.

With regard to inhibition of Cdk5/p25 activity with p5, upon the addition of the 24 amino acid polypeptide, p5, we observed a strong reduction in Cdk5/p25 activity. A plausible structure of the complex formed between p5 and Cdk5/p25 is shown in FIG. 13c. However, the molecular and regulatory mechanism of p5 action on Cdk5/p25 activity is still under investigation. As in FIG. 13b, the measurements were performed with a Cdk5/p25 concentration of 18.5 nM and a histone concentration of 25.4 μM. FIG. 13d shows the change in $V_{PID}$ when the p5 concentration ([p5]) was increased from 0.25 μM to 1.2 μM. From the figure, we can clearly see the effect of p5-based inhibition. Furthermore, the measurements agree with previous results of the interaction of p5 with the Cdk5/p25 complex obtained using a γ-$^{32}$P-ATP assay. In particular, the sharp decrease in Cdk5/p25 activity past [p5]=0.7 μM. This decrease is indicative of a specific threshold for p5 inhibition and will be studied further in future work.

We show that the operation of commercially sourced nFETs can be optimized to achieve a pH resolution of (7.2±0.3)×10$^{-3}$, ≈3-fold better than traditional ISFETs, and on par with solid-state dg2DFETs with an intrinsic gain α=8. Furthermore, the improved performance is attained when the devices are operated in a remote configuration, with the pH sensing element located off-chip and connected electrically to the FET. This is in contrast to conventional ISFETs which use integrated pH sensing membranes that form the gate dielectric. Our design greatly increases the versatility of nFETs, allowing them to be rapidly and easily interfaced with different biochemical sensors. The improved performance of the nFETs, operated in a remote configuration, was shown to be adequate to measure the activity of a pathological form of the proline directed kinase, Cdk5, which has been implicated to cause numerous neurodegenerative conditions including Alzheimer's disease. We further confirmed, using nFET measurements, the effectiveness of a custom polypeptide, p5, in re-regulating Cdk5 function. Together the measurements demonstrate performance of sensitive bioanalytical measurements using commercially available FETs.

Figure 17:
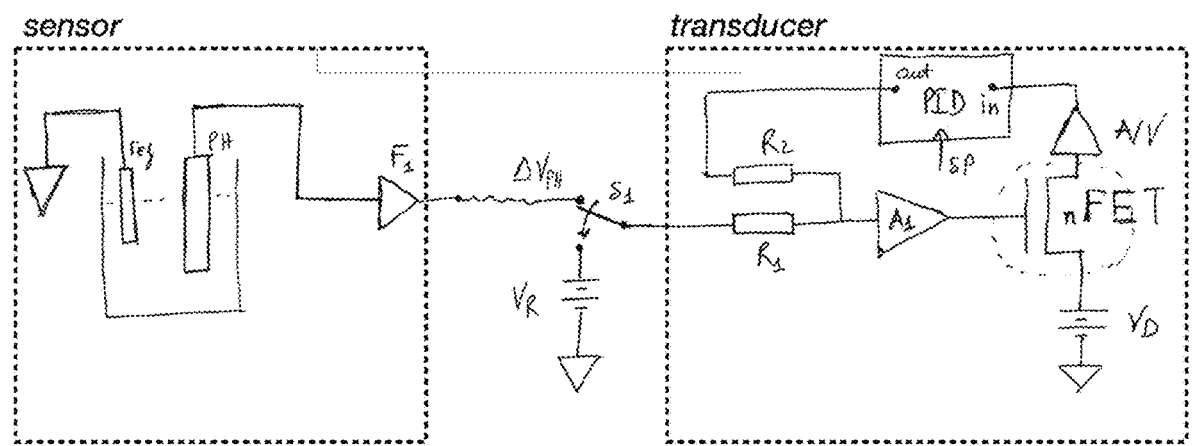
FIG. 17 shows a functional diagram of a remote biosensing configurations using silicon field-effect transistors.

Remote measurements include a sensor (e.g., pH sensing element) physically separated from the charge transduction element but connected electrically that improves system stability but can suffer from signal degradation due to stray parasitic interference. The setup in FIG. 17 overcomes some of the limitations of remote sensor configurations, for example when the sensor is not in close proximity to the transducer. In these cases, we place an ultra-low noise voltage follower (F1) with an input impedance that exceeds 100 GΩ, in close proximity with the sensing element to minimize charge degradation along the wire connecting the sensor to the transducer. The signal from the sensor is connected to a switch (S1) that is used to isolate the transducer from the sensor. In one version, the sensor signal ($\Delta V_{pH}$) is summed with the output of the PID controller using an adder (A1) and then applied to the FET gate. In a second version, the PID output is used to bias the reference electrode (Ref). The difference in voltage between the reference and pH electrodes is then applied to the FET gate. The PID operation to maintain the FET in a constant current mode is identical to the setup described in FIG. 7.

Figure 18:
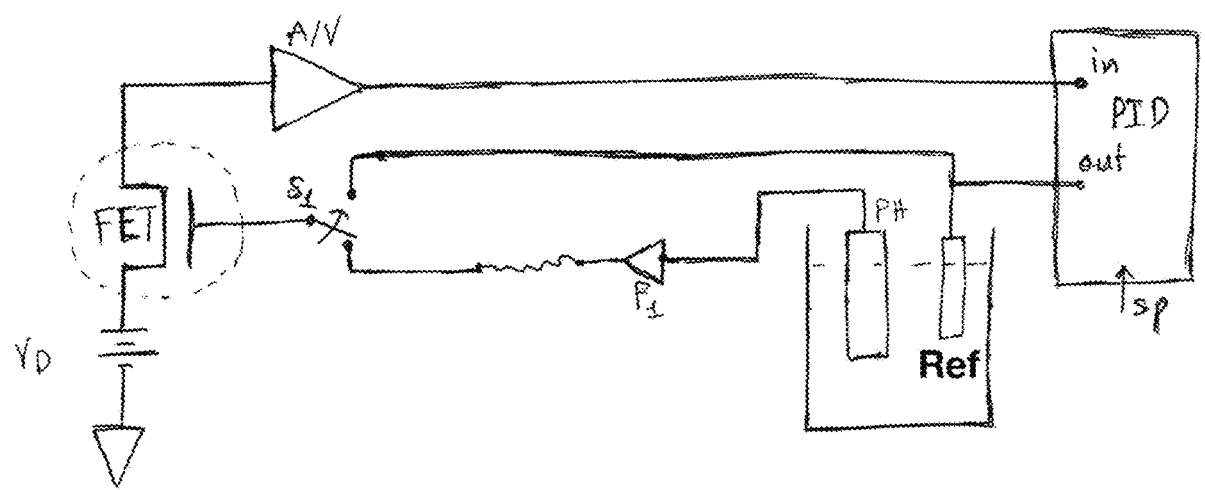
FIG. 18 shows a functional diagram of a remote biosensing configuration with an isolation element.

For integrated sensor and readout systems such as ion sensitive field-effect transistors (ISFETs) or chemical field-effect transistors (chemFETs), closed loop control can be used to improve measurement resolution using the setup seen in FIG. 18. In this case, a voltage applied to the reference electrode (ref) will change the current in the channel ($I_D$) spanning the source (S) and drain (D) electrodes. The output of the PID controller is used to continually adjust voltage applied to the reference electrode immersed in the solution bath to maintain a constant $I_D$ in response to chemical species adsorbing to the sensing surface.

Figure 19:
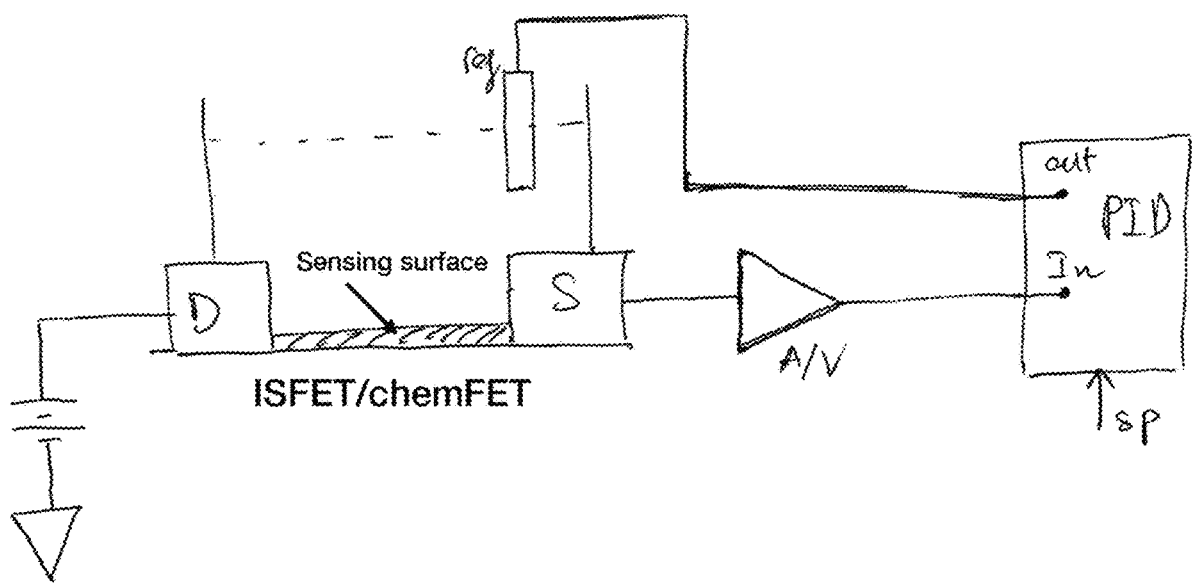
FIG. 19 shows a functional diagram of closed-loop feedback of ion-sensitive field-effect transistors (ISFETs) or other chemical field-effect transistors (chemFETs)
Figure 20:
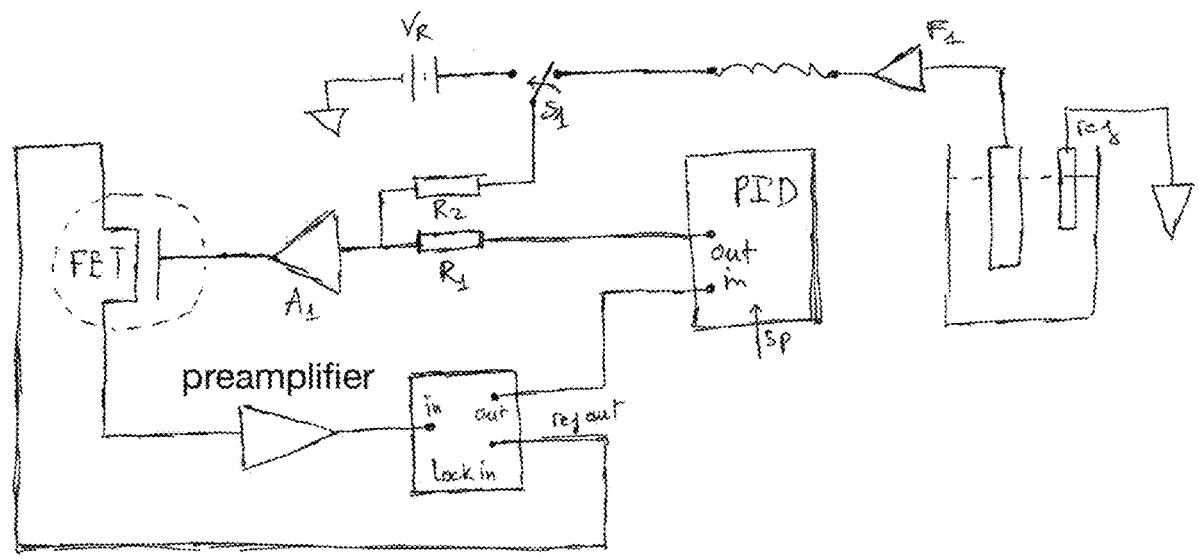
FIG. 20 shows a lock-in detection scheme to improve the signal-to-noise (SNR) ratio of biochemical sensing.

Measurement sensitivity can be improved by orders of magnitude by performing an AC measurement using phase sensitive detection (PSD) embedded within the measurement. The modifications to the transducer setup to achieve this are shown in FIG. 19. As shown in the figure, a reference AC voltage with a known frequency ($F_{AC}$) and amplitude ($V_{AC}$) is added to $V_D$. The applied AC voltage results in an AC component in $I_D$. Unlike the DC configuration in FIG. 17, the output of the current preamplifier is first input to a lock-in detector. The input signal is demodulated using two independent demodulators each operating using a reference signal separated by a phase angle of 90 degrees. This two-phase approach returns a demodulated DC signal that equals R=$I_D$×G, where G is the gain of the current preamplifier. The output of the lock-in amplifier is then connected to the PID input as described in FIG. 7. The lock-in detection scheme shown in FIG. 19 can be implemented without modification for the system in FIG. 18.

While one or more embodiments have been shown and described, modifications and substitutions may be made thereto without departing from the spirit and scope of the invention. Accordingly, it is to be understood that the present invention has been described by way of illustrations and not limitation. Embodiments herein can be used independently or can be combined.

All ranges disclosed herein are inclusive of the endpoints, and the endpoints are independently combinable with each other. The ranges are continuous and thus contain every value and subset thereof in the range. Unless otherwise stated or contextually inapplicable, all percentages, when expressing a quantity, are weight percentages. The suffix "(s)" as used herein is intended to include both the singular and the plural of the term that it modifies, thereby including at least one of that term (e.g., the colorant(s) includes at least one colorants). "Optional" or "optionally" means that the subsequently described event or circumstance can or cannot occur, and that the description includes instances where the event occurs and instances where it does not. As used herein, "combination" is inclusive of blends, mixtures, alloys, reaction products, and the like.

As used herein, "a combination thereof" refers to a combination comprising at least one of the named constituents, components, compounds, or elements, optionally together with one or more of the same class of constituents, components, compounds, or elements.

All references are incorporated herein by reference.

The use of the terms "a" and "an" and "the" and similar referents in the context of describing the invention (especially in the context of the following claims) are to be construed to cover both the singular and the plural, unless otherwise indicated herein or clearly contradicted by context. "Or" means "and/or." It should further be noted that the terms "first," "second," "primary," "secondary," and the like herein do not denote any order, quantity, or importance, but rather are used to distinguish one element from another. The modifier "about" used in connection with a quantity is inclusive of the stated value and has the meaning dictated by the context (e.g., it includes the degree of error associated with measurement of the particular quantity). The conjunction "or" is used to link objects of a list or alternatives and is not disjunctive; rather the elements can be used separately or can be combined together under appropriate circumstances.

What is claimed is:

1. A closed-loop controlled chemical apparatus comprising:
    a compound sensor comprising:
        an analyte sensor and that:
            produces, by the analyte sensor, a voltage signal that varies in response to an analyte that electrically perturbs the analyte sensor, such that an electrical perturbation changes the voltage signal from a target voltage, the voltage signal referenced to a reference voltage provided by a reference sensor through a composition comprising the analyte;
        the reference sensor in electrical communication with the analyte sensor through the composition and that:
            receives a feedback control signal from a feedback controller;
            actively nulls the difference between the voltage signal and the target voltage when the analyte sensor is perturbed by the analyte to maintain the analyte sensor at the target voltage for suppression of electrical noise fluctuations in the closed-loop controlled chemical apparatus that affect the voltage signal;
    a transistor comprising a gate terminal that is in electrical communication with the analyte sensor, such that:
        the gate terminal receives a gate potential such that a drain current of the transistor is maintained at a constant value in response to receipt of the feedback control signal by the reference sensor, such that the transistor is operated at an optimal transduction condition comprising peak sensitivity of the transistor and minimum noise of the transistor based on the feedback control signal;
    the feedback controller in electrical communication with the transistor and that:
        receives a transduction signal;
        determines a deviation of the transduction signal from a setpoint, the setpoint determined by transfer characteristics of the transistor;
        produces the feedback control signal that minimizes the deviation of the transduction signal from the setpoint based on a control model; and
        communicates the feedback control signal to the reference sensor for suppression of electrical noise fluctuations in the closed-loop controlled chemical apparatus.

2. The closed-loop controlled chemical apparatus of claim 1, wherein the transduction signal comprises the drain current from the transistor.

3. The closed-loop controlled chemical apparatus of claim 1, further comprising a phase-sensitive detector in electrical communication with the transistor such that:
    an input terminal of the phase-sensitive detector is in electrical communication with a drain terminal of the transistor and that receives the drain current from the drain terminal; and
    an output terminal of the phase-sensitive detector is in electrical communication with a source terminal of the transistor and that communicates an oscillating voltage to the source terminal, such that the phase-sensitive detector:
        compares the drain current to the oscillating voltage and produces a direct current signal that is proportional to a phase difference between the drain current and the oscillating voltage; and
        communicates the direct current signal to the feedback controller as the transduction signal.

4. The closed-loop controlled chemical apparatus of claim 1, wherein the gate potential comprises the voltage signal from the analyte sensor.

5. The closed-loop controlled chemical apparatus of claim 1, further comprising a summer in electrical communication with the analyte sensor, the feedback controller, and the gate terminal and that:
    receives the feedback control signal from the feedback controller;
    receives the voltage signal from the analyte sensor; and
    sums the feedback control signal and the voltage signal to produce the gate potential; and
    communicates the gate potential to the gate terminal.

6. The closed-loop controlled chemical apparatus of claim 1, wherein the transistor comprises a field-effect transistor.

7. The closed-loop controlled chemical apparatus of claim 1, wherein the analyte comprises a pathological form of a protein.

8. The closed-loop controlled chemical apparatus of claim 7, wherein the protein comprises an enzyme implicated in Alzheimer's disease.

9. The closed-loop controlled chemical apparatus of claim 1, wherein the analyte comprises a therapeutic agent that restores a nonpathological function of a pathogenic form of a protein.

10. The closed-loop controlled chemical apparatus of claim 1, wherein the closed-loop controlled chemical apparatus has a pH resolution of $3.5 \times 10^{-3}$ pH units that is more than three times greater than a pH resolution of an ion-sensitive field-effect transistor operated in absence of the feedback control signal.

11. A process for performing closed-loop control of the closed-loop controlled chemical apparatus of claim 1, the process comprising:
producing, by the analyte sensor, the target voltage;
contacting the analyte sensor and the reference sensor with the composition;
electrically perturbing, by the analyte in the composition, the analyte sensor;
changing, in response to the electrical perturbation, the voltage signal from the target voltage;
receiving, by the reference sensor, the feedback control signal from the feedback controller;
actively nulling, by the reference sensor, the voltage signal when the analyte sensor is electrically perturbed by the analyte to maintain the analyte sensor at the target voltage for suppression of electrical noise fluctuations in the closed-loop controlled chemical apparatus that affect the voltage signal;
receiving, by the gate terminal of the transistor, the gate potential such that the drain current of the transistor is maintained at the constant value in response to receipt of the feedback control signal by the reference sensor, wherein the transistor is operated at an optimal transduction condition comprising peak sensitivity of the transistor and minimum noise of the transistor based on the reference sensor;
receiving, by the feedback controller, the transduction signal;
determining the setpoint from transfer characteristics of the transistor;
determining, by the feedback controller, the deviation of the transduction signal from the setpoint;
producing, by the feedback controller, the feedback control signal that minimizes the deviation of the transduction signal from the setpoint based on the control model; and
communicating the feedback control signal from the feedback controller to the reference sensor and suppressing the electrical noise fluctuations to perform closed-loop control of the closed-loop controlled chemical apparatus.

12. The process of claim 11, wherein the transduction signal comprises the drain current from the transistor.

13. The process of claim 11, further comprising:
receiving, by an input terminal of a phase-sensitive detector that is in electrical communication with a drain terminal of the transistor, the drain current from the drain terminal;
communicating, by an output terminal of the phase-sensitive detector that is in electrical communication with a source terminal of the transistor, an oscillating voltage to the source terminal;
comparing, by the phase-sensitive detector, the drain current to the oscillating voltage;
producing, by the phase-sensitive detector, a direct current signal that is proportional to a phase difference between the drain current and the oscillating voltage; and
communicating the direct current signal to the feedback controller as the transduction signal.

14. The process of claim 11, wherein the gate potential comprises the voltage signal from the analyte sensor.

15. The process of claim 11, further comprising:
receiving, by a summer in electrical communication with the analyte sensor, the feedback controller, and the gate terminal, the feedback control signal from the feedback controller;
receiving, by the summer, the voltage signal from the analyte sensor;
summing, by the summer, the feedback control signal and the voltage signal to produce the gate potential; and
communicating the gate potential from the summer to the gate terminal.

16. The process of claim 11, wherein the transistor comprises a field-effect transistor.

17. The process of claim 11, wherein the analyte comprises a pathological form of a protein.

18. The process of claim 17, wherein the protein comprises an enzyme implicated in Alzheimer's disease.

19. The process of claim 11, wherein the analyte comprises a therapeutic agent that restores a nonpathological function of a pathogenic form of a protein.

20. The process of claim 11, wherein the closed-loop controlled chemical apparatus has a pH resolution that is at least three times greater than a pH resolution of an ion-sensitive field-effect transistor operated in absence of the feedback control signal.

* * * * *